US009655844B2

(12) United States Patent
Gerecht et al.

(10) Patent No.: US 9,655,844 B2
(45) Date of Patent: *May 23, 2017

(54) BIOCOMPATIBLE POLYSACCHARIDE-BASED HYDROGELS

(75) Inventors: Sharon Gerecht, Baltimore, MD (US); Yu-I Shen, Baltimore, MD (US); Chia Chi Ho, Baltimore, MD (US); Guoming Sun, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 168 days.

This patent is subject to a terminal disclaimer.

(21) Appl. No.: 13/140,324

(22) PCT Filed: Dec. 17, 2009

(86) PCT No.: PCT/US2009/068479
§ 371 (c)(1),
(2), (4) Date: Jun. 16, 2011

(87) PCT Pub. No.: WO2010/078036
PCT Pub. Date: Jul. 8, 2010

(65) Prior Publication Data
US 2011/0275565 A1    Nov. 10, 2011

Related U.S. Application Data

(60) Provisional application No. 61/138,335, filed on Dec. 17, 2008.

(51) Int. Cl.
*A61K 47/36* (2006.01)
*C08B 37/02* (2006.01)
(Continued)

(52) U.S. Cl.
CPC ............... *A61K 9/06* (2013.01); *A61K 47/36* (2013.01); *C08B 37/00* (2013.01);
(Continued)

(58) Field of Classification Search
None
See application file for complete search history.

(56) References Cited

U.S. PATENT DOCUMENTS 5,334,640 A * 8/1994 Desai et al. ............... 524/56
5,591,709 A    1/1997 Lindenbaum
(Continued)

FOREIGN PATENT DOCUMENTS

WO    WO-03/072155 A1    9/2003
WO    WO-2006/060779 A2    6/2006
(Continued)

OTHER PUBLICATIONS

Y Zhang, CY Won, CC Chu. "Synthesis and Characterization of Biodegradable Hydrophobic-Hydrophilic Hydrogel Networks with a Controlled Swelling Property." Journal of Polymer Science: Part A: Polymer Chemistry. vol. 38, 2000, pp. 2392-2404.*
(Continued)

*Primary Examiner* — Isaac Shomer
(74) *Attorney, Agent, or Firm* — Venable LLP; Keith G. Haddaway; Miguel A. Lopez

(57) ABSTRACT

Modified polysaccharides and crosslinked modified polysaccharide compositions are described. Methods of using the crosslinked modified polysaccharide compositions to deliver proteins, oligonucleotides, or pharmaceutical agents are also disclosed.

31 Claims, 19 Drawing Sheets

(51) Int. Cl.
   *A61K 9/06*    (2006.01)
   *C08B 37/00*   (2006.01)
   *C08L 5/02*    (2006.01)
   *A61K 9/00*    (2006.01)

(52) U.S. Cl.
   CPC ............ *C08B 37/0021* (2013.01); *C08L 5/02* (2013.01); *A61K 9/0024* (2013.01); *Y10S 524/916* (2013.01)

(56) References Cited

U.S. PATENT DOCUMENTS

| | | | |
|---|---|---|---|
| 6,476,204 | B1 | 11/2002 | Kim et al. |
| 6,602,952 | B1 | 8/2003 | Bentley et al. |
| 7,799,767 | B2 | 9/2010 | Lamberti et al. |
| 2002/0081729 | A1 | 6/2002 | Peters et al. |
| 2004/0151752 | A1 | 8/2004 | Won et al. |
| 2006/0024357 | A1 | 2/2006 | Carpenter et al. |
| 2007/0167354 | A1* | 7/2007 | Kennedy et al. ............ 514/8 |
| 2008/0020015 | A1 | 1/2008 | Carpenter et al. |
| 2009/0022777 | A1 | 1/2009 | Mathiowitz et al. |
| 2009/0130755 | A1* | 5/2009 | Detamore et al. ............ 435/374 |
| 2009/0280182 | A1 | 11/2009 | Beck et al. |
| 2012/0225814 | A1 | 9/2012 | Hanjaya-Putra et al. |

FOREIGN PATENT DOCUMENTS

| | | |
|---|---|---|
| WO | WO-2008/098019 A2 | 8/2008 |
| WO | WO-2010/078036 A2 | 7/2010 |
| WO | WO-2011/060095 A2 | 5/2011 |
| WO | WO-2012003370 A2 | 1/2012 |
| WO | WO-2012/158312 A2 | 11/2012 |

OTHER PUBLICATIONS

J Maia, L Ferreira, R Carvalho, MA Ramos, MH Gil. "Synthesis and characterization of new injectable and degradable dextran-based hydrogels." Polymer, vol. 46, 2005, pp. 9604-9614.*

G Sun, CC Chang. "Synthesis, characterization of biodegradable dextran-allyl isocyanate-ethylamine/polyethylene glycol-diacrylate hydrogels and their in vitro release of albumin." Carbohydrate Polymers, vol. 65, 2006, pp. 273-287.*

CC Chu. "Chapter 19: Biodegradable Hydrogels as Drug Controlled Release Vehicles." Copyright 2004, pp. 1-39 (numbered by examiner). Available online at http://www.crcnetbase.com/doi/abs/10.1201/9780203913338.ch19, accessed Apr. 22, 2013.*

R Zhang, M Tang, A Bowyer, R Eisenthal, J Hubble. "0 A novel pH- and ionic-strength-sensitive carboxy methyl dextran hydrogel." Biomaterials, vol. 26, 2005, pp. 4677-4683.*

L Lombardo, R Reeves, A Ribeiro, JB Leach. "Crosslinked Carboxymethylcellulose Hydrogels: Versatile Platforms for Studying Cellular Behavior in 3D Biomaterials." Transactions of the 32$^{nd}$ Annual Meeting of the Society for Biomaterials, vol. 30:25, 2007, Annual Meething. http://jleachlab.org/people/lombardo.html (May 12, 2015). 2 printed pages.*

HyClone Thermo Scientific. Materials Safety Data Sheet for Poly(Ethylene Glycol) Diacrylate. https://static.thermoscientific.com/images/D02114~.pdf, accessed Feb. 8, 2016. Created Nov. 10, 2009, 7 printed pages.*

Azzam et al., 2003 Dextran-spermine conjugate: an efficient vector for gene delivery. Macromol. Symp. vol. 195, p. 247-261.

Chung et al. 2003 Poly(ethylene glycol)-grafted poly(3-hydroxyundecenoate) networks for enhanced blood compatibility. International Journal of Biological Macromolecules, vol. 32, pp. 17-22.

De Jong et al., 2000 Novel self-assembled hydrogels by stereocomplex formation in aqueous solution of enantiomeric lactic acid oligomers grafted to dextran. Macromolecules, vol. 33, pp. 3680-3686.

Edman et al., 1980 Immobilization of proteins in microspheres of biodegradable polyacruldextran. Joural of Pharmaceutical Sciences, vol. 69, No. 7. pp. 838-842.

Ferreira et al., 2007 Bioactive hydrogel scaffolds for controllable vascular differentiation of human embryonic stem cells. Biomaterials, vol. 28, pp. 2706-2717.

Gerecht et al., 2007 Hyaluronic acid hydrogel for controlled self-renewal and differentiation of human embryonic stem cells. Proc Natl Acad Sci USA, vol. 104, No. 27, pp. 11298-11303.

Gerecht et al., 2007 The effect of actin disrupting agents on contact guidance of human embryonic stem cells. Biomaterials, vol. 28, pp. 4068-4077.

Greenwald et al., 2003 Effective drug delivery by PEGylated drug conjugates. Advanced Drug Delivery Reviews, vol. 55, pp. 217-250.

Guo et al., 2005 Synthesis and characterization of novel biodegradable unsaturated poly(ester amide)/poly(ethylene glycol) diacrylate hydrogels. Journal of Polymer Science Part A-Polymer Chemistry, vol. 43, No. 17, pp. 3932-3944.

Guo et al., 2007 Biodegradation of unsaturated poly(ester-amide)s and their hydrogels. Biomaterials, vol. 28, pp. 3284-3294.

Heinze et al., 2006 Functional polymers based on dextran. Springer-Verlag Berlin Heidelberg, vol. 205, pp. 199-291. (Table of contents only).

Hern et al., 1998 Incorporation of adhesion peptides into nonadhesive hydrogels useful for tissue resurfacing. John Wiley & Sons. Inc. vol. 39. p. 266.

Hu et al., 2002 Bioactivities of ricin retained and its immunoreactivity to anti-ricin polyclonal antibodies alleviated through pegylation. The International Journal of Biochemistry & Cell Biology, vol. 34, pp. 396-402.

International Search Report issued for PCT/US2009/068479 dated Sep. 2, 2010.

Ito et al., 2007 Dextran-based in situ cross-linked injectable hydrogels to prevent peritoneal adhesions. Biomaterials, vol. 28, pp. 3418-3426.

Kim et al., 2000 In vitro release behavior of dextran-methacrylate hydrogels using doxorubicin and other model compounds. Journal of Biomaterials Applications, vol. 15, p. 23.

Kim et al., 2000 Pore structure analysis of swollen dextran-methacrylate hydrogels by SEM and mercury intrusion porosimetry. Fiber and Polymer Science Program, vol. 53, pp. 258-266.

Kim et al., 2001 Albumin release from biodegradable hydrogels composed of dextran and poly(ethylene glycol) macromer. Arch Pharma. Res., vol. 24, No. 1, pp. 69-73.

Kopecek et al., 2002 Swell gels. Nature Publishing Group, vol. 417, pp. 388-391.

Koumenis et al., 2000 Modulating pharmacokinetics of an anti-interleukin-8 F(ab')2 by amine-specific PEGylation with preserved bioactivity. International Journal of Pharmaceutics, vol. 198, pp. 83-95.

Maia et al., 2005 Synthesis and characterization of new injectable and degradable dextran-based hydrogels. Polymer, vol. 46, pp. 9604-9614.

Massia et al., 2002 Surface-immobilized dextran limits cell adhesion and spreading. Biomaterials, vol. 21, pp. 2253-2261.

Muslim et al., 2001 Synthesis and bioactivities of poly(ethylene glycol)-chitosan hybrids. Carbohydrate Polymers, vol. 46. pp. 323-330.

Peppas et al., 1985 The structure of highly crosslinked poly(2-hydroxyethyl methacrylate) hydrogels. Journal of Biomedical Materials Research, vol. 19, pp. 397-411.

Peppas et al., 2000 Hydrogels in pharamaceutical formulations. European Journal of Pharmaceutics and Biopharmaceutics, vol. 50, pp. 27-46.

Sun etal., 2006 Synthesis, characterization of biodegradable dextran-allyl isocyanate-ethylamine/polyethylene glycol-diacrylate hydrogels and their in vitro release of albumin. Carbohydrate Polymers, vol. 65, No. 3, pp. 273-287.

Sun et al., 2009 Effects of precursor and cross-linking parameters on the properties of dextran-allyl isocyanate-ethylamine/poly(ethylene glycol diacrylate) biodegradable hydrogels and their release of ovalbumin. Journal of Biomaterials Science, vol. 20, pp. 2003-2022.

(56) References Cited

OTHER PUBLICATIONS

Van Dijk-Wolthuis et al., 1995 Synthesis, characterization, and polymerization of glycidyl methacrylate derivatized dextran. Macromolecules, vol. 28, pp. 6317-6322.
Van Dijk-Wolthuis et al., 1997 A new class of polymerizable dextrans with hydrolyzable groups: hydroxyethyl methacrylated dextran with and without oligolactate spacer. Polymer, vol. 38, No. 25, pp. 6235-6242.
Van Dijk-Wolthuis et al., 1997 Degradation and release behavior of dextran-based hydrogels. Macromolecules, vol. 30, pp. 4639-4645.
Van Tomme et al., 2006 Degradation behavior of dextran hydrogels composed of positively and negatively charged microspheres. Biomaterials, vol. 27, pp. 4141-4148.
Van Tomme et al., 2007 Biodegradable dextran hydrogels for protein delivery applications. Future Drugs Ltd., vol. 4, No. 2, pp. 147-164.
Wang et al., 2002 A tough biodegradable elastomer. Nature Biotechnology, vol. 20, No. 6, pp. 602-606.
Wang et al., 2002 Plasma-induced immobilization of poly(ethylene glycol) onto poly(vinylidene fluoride) microporous membrane. Journal of Membrane Science, vol. 195, pp. 103-114.
Wang et al., 2003 In vivo degradation characteristics of poly(glycerol sebacate). Journal of Biomedical Materials Research, vol. 66A, No. 1, pp. 192-197.
Won et al., 1998 Dextran-estrone conjugate: synthesis and in vitro release study. Carbohydrate Polymers, vol. 36, pp. 327-334.
Won et al., 2000 II. Starch. Biomaterials & Engineering Handbook, D. L. Wise, p. 356.
Zhang et al., 2003 Novel Biodegradable and thermosensitive DEX-Al/PNIPAAm hydrogel. Macromolecular Bioscience, vol. 3, pp. 87-91.
Zhang et al., 1999 Synthesis and characterization of biodegradable network hydrogels having both hydrophobic and hydrophilic components with controlled swelling behavior. Journal of Polymer Science, vol. 37, pp. 4554-4569.
Zhang et al., 2002 In vitro release behavior of insulin from biodegradable hybrid hydrogel networks of polysaccharide and synthetic biodegradable polyester, Journal of biomaterials Applications, vol. 16, p. 305.
Zhang et al., 2002 Properties and biocompatibility of chitosan films modified by blending with PEG. Biomaterials, vol. 23, p. 2641-2648.
Zhang et al., 2004 Temperature sensitive dendrite-shaped PNIPAAm/Dex-Al hybrid hydrogel particles: formulation and properties. European Polymer Journal, vol. 40, pp. 2251-2257.
Adams et al., "Stem Cell Therapy for Vascular Disease," Trends in Cardiovascular Medicine, vol. 17, No. 7,pp. 246-251, 2007.
Aicher et al., "Mobilizing Endothelial Progenitor Cells," Hypertension, vol. 45, pp. 321-325, 2005.
Asahara et al., "Bone Marrow Origin of Endothelial Progenitor Cells responsible for Postnatal Vasculogenesis in Physiological and Pathological Neovascularization," Circ. Res., vol. 85, pp. 221-228, 1999.
Asahara et al., "Isolation of Putative Progenitor Endothelial Cells for Angiogenesis," Science, vol. 275, pp. 964967, 1997.
Asahara et al., "Synergistic Effect of Vascular Endothelial Growth Factor and Basic Fibroblast Growth Factor on Angiogenesis in Vivo," Circulation, vol. 92, No. 9, pp. 365-371, 1995.
Au et al., "Bone marrow-derived mesenchymal stem cells facilitate engineering of long-lasting functional vasculature," Blood, vol. 111, No. 9, pp. 4551-4558, 2008.
Au et al., "Differential in vivo potential of endothelial progenitor cells from human umbilical cord blood and adult peripheral blood to form functional long-lasting vessels," Blood, vol. 111, pp. 1302-1305, 2008.
Banfi et al., "Critical Role of Microenvironmental Factors in Angiogenesis," Cuff Atheroscler Rep, vol. 7, No. 3, pp. 227-234, 2005.
Bayless et al., "RGD-Dependent Vacuolation and Lumen Formation Observed during Endothelial Cell Morphogenesis in Three-Dimensional Fibrin Matrices Involves the $\alpha_v\beta_3$ and $\alpha_5\beta_1$ Integrins," Am. J. Pathol., vol. 156, No. 5, pp. 1673-1683, 2000.
Bayless et al., "The Cdc42 and Rac1 GTPases are required for capillary lumen formation in three-dimensional extracellular matrices," J. Cell Sci., vol. 115, pp. 1123-1136, 2002.
Bettinger et al., "Enhancement in IN Vitro Capillary Tube Formation by Substrate Nanotopography," Adv. Mater., vol. 20, pp. 99-103, 2008.
Bos et al., "Tissue reactions of in situ formed dextran hydrogels crosslinked by stereocomplex formation after subcutaneous implantation in rats," Biomaterials, vol. 26, No. 18, pp. 3901-3909, 2005.
Boudou et al., "An extended relationship for the characterization of Young's modulus and Poisson's ratio of tunable polyacrylamide gels," Biorheology, vol. 43, pp. 721-728, 2006.
Burdick et al., "Controlled Degradation and Mechanical Behavior of Photopolymerized Hyaluronic Acid Networks," Biomacromolecules, vol. 6, No. 1, pp. 386-391, 2005.
Cao et al., "The influence of architecture on degradation and tissue ingrowth into three-dimensional poly(lactic-co-glycolic acid) scaffolds in vitro and in vivo," Biomaterials, vol. 27, No. 14, pp. 2854-2864, 2006.
Chen et al., "Disruption of Ang-1/Tie-2 Signaling Contributes to the Impaired Myocardial Vascular Maturation and Angiogenesis in Type II Diabetic Mice," Arterioscler Thromb Vasc Biol, vol. 28, No. 9, pp. 1606-1613, 2008.
Chen et al., "Geometric Control of Cell Life and Death," Science, vol. 276, pp. 1425-1428, 1997.
Chiu et al., "Scaffolds with covalently immobilized VEGF and Angiopoietin-1 for vascularization of engineered tissues," Biomaterials, vol. 31, p. 226-241, 2009.
Chun et al., "MT1-MMP-dependent neovessel formation within the confines of the three-dimensional extracellular matrix," J. Cell. Biol., vol. 167, pp. 757-767, 2004.
Collen et al., "Membrane-type matrix metalloproteinase-mediated angiogenesis in a fibrin-collagen matrix," Blood, vol. 101, pp. 1810-1817, 2003.
Critser et al., "Collagen matrix physical properties modulate endothelial colony forming cell-derived vessels in vivo," Microvascular Research, vol. 80, pp. 23-30, 2010.
Davis et al., "An $\alpha2\beta1$ Integrin-Dependent Pinocytic Mechanism Involving Intracellular Vacuole Formation and Coalescence Regulates Capillary Lumen and Tube Formation in Three-Dimensional Collagen Matric," Exp. Cell. Res., vol. 224, pp. 39-51, 1996.
Davis et al., "Endothelial Extracellular Matrix: Biosynthesis, Remodeling, and Functions During Vascular Morphogenesis and Neovessel Stabilization," Circ Res., vol. 97, pp. 1093-1107, 2005.
Davis et al., "Extracellular matrix mediates a molecular balance between vascular morphogenesis and regression," Current Opinion in Hematology, vol. 15, No. 3, pp. 197-203, 2008.
Davis et al., "Mechanisms Controlling Human Endothelial Lumen Formation and Tube Assembly in Three-Dimensional Extracellular Matrices," Birth Defects Research Part C-Embryo Today: Reviews, vol. 81, No. 4, pp. 270-285, 2007.
Davis et al., "Regulation of Endothelial Cell Morphogenesis by Integrins, Mechanical Forces, and Matrix Guidance Pathways," Exp. Cell Res., vol. 216, pp. 113-123, 1995.
Davis, "The development of the vasculature and its extracellular matrix: a gradual process defined by sequential cellular and matrix remodeling events," Am. J. Physiol. Heart Circ. Physiol., vol. 299, pp. H245-H247, 2010.
Delafontaine et al., "Expression, Regulation, and Function of IGF-1, IGF-1R, and IGF-1 Binding Proteins in Blood Vessels," Arterioscler Thromb Vasc Biol, vol. 24, No. 3, pp. 435-444, 2004.
Deroanne et al., "In vitro tubulogenesis of endothelial cells by relaxation of the coupling extracellular matrix-cytoskeleton," Cardiovasc. Res., vol. 49, pp. 647-658, 2001.
Discher et al., "Tissue Cells Feel and Respond to the Stiffness of Their Substrate," Science, vol. 310, pp. 1139-1143, 2005.
Dvir et al., "Prevascularization of cardiac patch on the omentum improves its therapeutic outcomes," Proc Natl Acad Sci U S A, vol. 106, No. 35, pp. 14990-14995, 2009.

(56) References Cited

OTHER PUBLICATIONS

Ehrbar et al., "Cell-Demanded Liberation of VEGF121 From Fibrin Implants Induces Local and Controlled Blood Vessel Growth," *Circ Res*, vol. 94, No. 8, pp. 1124-1132, 2004.
Elia et al., "Stimulation of in vivo angiogenesis by in situ cross-linked, dual growth factor-loaded, glycosaminoglycan hydrogels," *Biomaterials*, vol. 31, No. 17, pp. 4630-4638, 2010.
Engler et al., "Matrix Elasticity Directs Stem Cell Lineage Specification," *Cell*, vol. 126, pp. 677-689, 2006.
Fan et al., "Vegf blockage inhibits angiogenesis and reepithelialization of endometrium," *FASEB J*, vol. 22, No. 10, pp. 3571-3580, 2008.
Ferreira et al., "Vascular Progenitor Cells Isolated From Human Embryonic Stem Cells Give Rise to Endothelial and Smooth Muscle-Like Cells and Form Vascular Networks in Vivo," *Circ. Res.*, vol. 101, pp. 286-294, 2007.
Fleissner et al., "The IGF-1 Receptor as a Therapeutic Target to Improve Endothelial Progenitor Cell Function," *Mol Med* vol. 14, No. 5-6, pp. 235-237, 2008.
Folkman et al., "Angiogenesis in vitro," *Nature*, vol. 288, pp. 551-556, 1980.
Galis et al., "Increased Expression of Matrix Metalloproteinases and Matrix Degrading Activity in Vulnerable Regions of Human Atherosclerotic Plaques," *J. Clin. Invest.*, vol. 94, pp. 2493-2503, 1994.
Galvez et al., "Membrane Type 1-Matrix Metalloproteinase Is Activated during Migration of Human Endothelial Cells and Modulates Endothelial Motility and Matrix Remodeling," *J. Biol. Chem.*, vol. 276, pp. 37491-37500, 2001.
Genasetti et al., "Hyaluronan and Human Endothelial Cell Behavior," *Connect. Tissue Res.*, vol. 49, No. 3, pp. 120-123, 2008.
Ghosh et al., "Cell adaptation to a physiologically relevant ECM mimic with different viscoelastic properties," *Biomaterials*, vol. 28, pp. 671-679, 2007.
Gobin et al., "Cell migration through defined, synthetic extracellular matrix analogues," *FASEB J.*: 01-0759fje, pp. 1-16, 2002.
Gong et al., "Double-Network Hydrogels with Extremely High Mechanical Strength," *Adv Mater*, vol. 15, No. 14, pp. 1155-1158, 2003.
Guiducci et al., "Mechanisms of vascular damage in SSc-implications for vascular treatment strategies," *Rheumatology*, vol. 47, suppl. 5, pp. v18-v20, 2008.
Haas, "Endothelial cell regulation of matrix metalloproteinases," *Can. J. Physiol. Pharmacol.*, vol. 83, pp. 1-7, 2005.
Han et al., "TNF-α stimulates activation of pro-MMP2 in human skin through NF-κb mediated induction of MT1-MMP," *Journal of Cell Science*, vol. 114, pp. 131-139, 2001.
Hanjaya-Putra et al., "Vascular endothelial growth factor and substrate mechanics regulate in vitro tubulogenesis of endothelial progenitor cells," *Journal of Cellular and Molecular Medicine*, vol. 14, No. 10, pp. 2436-2447, 2010.
Hanjaya-Putra et al., "Vascular Engineering Using Human Embryonic Stem Cells," *Biotechnology Progress*, 2009, vol. 25, Iss. 1, pp. 2-6.
Hasan et al., "Adaptation to oxygen deprivation in cultures of human pluripotent stem cells, endothlial progenitor cells, and umilical vein endothelial cells", *Am J Physiol Cell Physiol.*, vol. 298, p. C1527-C1537, 2010.
Hennick et al. "Novel crosslinking methods to design hydrogels," *Adv. Drug Deli. Rev.*, vol. 54, No. 1, pp. 13-36, 2002.
Hill et al., "Circulating Endothelial Progenitor Cells, Vascular Function and cardiovascular Risk," *New England J. Med.*, vol. 348, pp. 593-600, 2003.
Hirschi et al., "Assessing Identity, Phenotype, and Fate of Endothelial Progenitor Cells," *Arterioscler. Thromb. Vasc. Biol.*, vol. 28, pp. 1584-1595, 2008.
Hosack et al., "Microvascular maturity elicited in tissue treated with cytokine-loaded hyaluronan-based hydrogels," *Biomaterials*, vol. 29, No. 15, 2336-47, 2008.
Ingber et al., "How Does Extracellular Matrix Control Capillary Morphogenesis?" *Cell*, vol. 58, pp. 803-805, 1989.
Ingber et al., "Mechanochemical Switching between Growth and Differentiation during Fibroblast Growth Factor-stimulated Angiogenesis in Vitro: Role of Extracellular Matrix," *J. Cell Biol.*, vol. 109, pp. 317-330, 1989.
Ingber, "Mechanical Signaling and the Cellular Response to Extracellular Matrix in Angiogenesis and Cardiovascular Physiology," *Circ. Res.*, vol. 91, pp. 877-887, 2002.
Ingram et al., "Identification of a novel hierarchy of endothelial progenitor cells using human peripheral and umbilical cord blood," *Blood*, vol. 104, pp. 2752-2760, 2004.
Ingram et al., "Vessel wall-derived endothelial cells rapidly proliferate because they contain a complete hierarchy of endothelial progenitor cells," *Blood*, vol. 105, No. 7, pp. 2783-2786, 2005.
International Search Report issued in Application No. PCT/US2010/056268 dated Jul. 28, 2011.
International Search Report issued in Application No. PCT/US2011/042671 dated Feb. 17, 2012.
Iruela-Arispe et al.,"Cellular and Molecular Mechanisms of Vascular Lumen Formation," *Dev Cell.*, vol. 16, pp. 222-231, 2009.
Ispanovic et al., "Cdc42 and RhoA have opposing roles in regulating membrane type 1-matrix metalloproteinase localization and matrix metalloproteinase-2 activation," *Am. J. Physiol. Cell Physiol.*, vol. 295, pp. C600-C610, 2008.
Jaffe et al., "Rho GTPases: Biochemistry and Biology," *Annu. Rev. Cell Dev. Biol.*, vol. 21, pp. 247-269, 2005.
Kamei et al., "Endothelial tubes assemble from intracellular vacuoles in vivo," *Nature*, vol. 442, pp. 453-456, 2006.
Kaya et al., "VEGF protects brain against focal ischemia without increasing blood-brain permeability when administered intracerebroventicularly,"*J. Cereb. Blood. Flow. Metab*, vol. 25, pp. 1111-1118, 2005.
Keskar et al., "Initial evaluation of vascular ingrowth into superporous hydrogels," *J Tissue Eng Regen Med*, vol. 3, No. 6, pp. 486-490, 2009.
Khetan et al., "Cellular Encapsulation in 3D Hydrogels for Tissue Engineering," *Vis. Exp.*, (32), pp. 1-4, 2009.
Khetan et al., "Sequential crosslinking to control cellular spreading in 3-dimensional hydrogels," *Soft Matter*, vol. 5, No. 8, pp. 1601-1606, 2009.
Khetan et al., "Tuning Hydrogel Properties for Applications in Tissue Engineering," *Conf. Proc. IEEE Eng. Med. Biol. Soc.*, vol. 1, pp. 2094-2096, 2009.
Kilarski et al., "Biomechanical regulation of blood vessel growth during tissue vascularization," *Nat. Med.*, vol. 15, pp. 657-664, 2009.
Kniazeva et al., "Endothelial cell traction and ECM density influence both capillary morphogenesis and maintenance in 3-D," *Am. J. Physiol. Cell Physiol.*, vol. 297, No. 1, pp. C179-187, May 2009.
Kraehenbuehl et al., "Cell-responsive hydrogel for encapsulation of vascular cells," *Biomaterials*, vol. 30, No. 26, pp. 4318-4324, 2009.
Langer, "New Methods of Drug Delivery," *Science*, vol. 249, No. 4976, pp. 1527-1533, 1990.
Lee et al., "Controlled growth factor release from synthetic extracellular matrices," *Nature*, vol. 408, No. 6815, pp. 998-1000, 2000.
Leslie-Barbick et al., "Covalently-lmmobolized Vascular Endothelial Growth Factor Promotes Endothelial Cell Tubulogensis in Poly(ethylene glycol) Diacrylate Hydrogels," *Journal of Biomaterials Science, Polymer Edition*, vol. 20, No. 12, pp. 1763-1779, 2009.
Li et al., "VEGF and PlGF promote adult vasculogenesis by enhancing EPC recruitment and vessel formation at the site of tumor neovascularization," *FASEB J.*, vol. 20, pp. 1495-1497, 2006.
Lo et al., "Cell Movement Is Guided by the Rigidity of the Substrate," *Biophys. J.*, vol. 79, pp. 144-152, 2000.
Lubarsky et al., "Tube Morphogenesis: Making and Shaping Biological Tubes," *Cell*, vol. 112, pp. 19-28, 2003.
Lutolf et al., "Synthetic biomaterials as instructive extracellular microenvironments for morphogenesis in tissue engineering," *Nature Biotechnology*, vol. 23, No. 1, pp. 47-55, 2005.
Lutolf et al., "Synthetic matrix metalloproteinase-sensitive hydrogels for the conduction of tissue regeneration: Engineering cell-invasion characteristics," *Proc. Natl. Acad. Sci. U S. A.*, vol. 100, No. 9, pp. 5413-5418, 2003.

(56) References Cited

OTHER PUBLICATIONS

Mammoto et al., "A mechanosenstivie transcriptional mechanism that controls angiogenesis," *Nature*, vol. 457, pp. 1103-1108, 2009.
Mammoto et al., "Rho signaling and mechanical control of vascular development,"*Curr. Opin. Hematol.*, vol. 15, pp. 228-234, 2008.
Matthews et al., "Cellular adaptation to mechanical stress: role of integrins, Pho, cytoskeletal tension and mechanosensitive ion channels," *J. Cell Sci.*, vol. 119, pp. 508-518, 2006.
McBeath et al., "Cell Shape, Cytoskeletal Tension, and RhoA Regulate Stem Cell Lineage Commitment", *Dev. Cell.*, vol. 6, pp. 483-495, 2004.
Mead et al., "Isolation and Characterization of Endothelial Progenitor Cells from Human Blood," *Current protocols in stem cell biology*, vol. 6, pp. 2C.1.1-2C.1.27, 2008.
Melero-Martin et al., "Engineering Robust and Functional Vascular Networks in Vivo With Human Adult and Cord Blood-Derived Progenitor Cells," *Circulation Research*, vol. 103, No. 2, pp. 194-202, 2008.
Mikos et al., "Prevascularization of Porous Biodegradable Polymers," *Biotechnol Bioeng*, vol. 42, No. 6, pp. 716-723, 1993.
Moon et al., "Biomimetic hydrogels with pro-angiogenic properties," *Biomaterials*, vol. 31, No. 14, pp. 3840-3847, 2010.
Moore et al., "Control of Basement Membrane Remodeling and Epithelial Branching Morphogenesis in Embryonic Lung by Rho and Cytoskeletal Tension," *Dev. Dyn.*, vol. 232, pp. 268-281, 2005.
Murphy et al., "Sustained release of vascular endothelial growth factor from mineralized poly(lactide-co-glycolide) scaffolds for tissue engineering," *Biomaterials*, vol. 21, No. 24, pp. 2521-2527, 2000.
Peattie et al., "Stimulation of in vivo angiogenesis by cytokine-loaded hyaluronic acid hydrogel implants," *Biomaterials*, vol. 25, No. 14, pp. 2789-2798, 2004.
Pelham et al., "Cell locomotion and focal adhesions are regulated by substrate flexibility," *Proc. Natl. Acad. Sci. U. S. A.*, vol. 94, pp. 13661-13665, 1997.
Perets et al., "Enhancing the vascularization of three-dimensional porous alginate scaffolds by incorporating controlled release basic fibroblast growth factor microspheres," *J Biomed Mater Res Part A*, vol. 65A, No. 4, pp. 489-497, 2003.
Perkins et al., "Conventional and Immunoelectron Microscopy of Mitchondria," *Methods Mol. Biol.*, vol. 372, pp. 467-483, 2007.
Petit et al., "The SDF-1-CXCR4 signaling pathway: a molecular hub modulating neo-angiogenesis," *Trends Immunol*, vol. 28, No. 7, pp. 299-307, 2007.
Phelps et al., "Bioartificial matrices for therapeutic vascularization," *Proc Natl Acad Sci U S A*, vol. 107, No. 8, pp. 3323-3328, 2010.
Pike et al., "Heparin-regulated release of growth factors in vitro and angiogenic response in vivo to implanted hyaluronan hydrogels containing VEGF and bFGF," *Biomaterials*, vol. 27, No. 30, pp. 5242-5251, 2006.
Prater et al., "Working hypothesis to redefine endothelial progenitor cells," *Leukemia*, vol. 21, pp. 1141-1149, 2007.
Prior et al., "What makes vessels grow with exercise training?" *J Appl Physiol*, vol. 97, No. 3, pp. 1119-1128, 2004.
Raeber et al., "Molecularly Engineered PEG Hydrogels: A Novel Model System for Proteolytically Mediated Cell Migration," *Biophysical Journal*, vol. 89, No. 2, pp. 1374-1388, 2005.
Rafii et al., "Therapeutic stem and progenitor cell transplantation for organ vascularization and regeneration," *Nat Med*, vol. 9, No. 6, pp. 702-712, 2003.
Ravi et al., "Biomaterials for vascular tissue engineering," *Regenerative Medicine*, vol. 5, No. 1, 107-20, 2010.
Richardson et al., "Polymeric system for dual growth factor delivery," *Nat Biotech*, vol. 19, No. 11, pp. 1029-1034, 2001.
Riley et al., "Stimulation of in vivo angiogenesis using dual growth factor-loaded crosslinked glycosaminoglycan hydrogels," *Biomaterials*, vol. 27, No. 35, pp. 5935-5943, 2006.
Romanic et al., "Matrix Metalloproteinase Expression Increases After Cerebral Focal lschemia in Rats: Inhibition of Matrix Metalloproteinase-9 Reduces Infarct Size," *Stroke*, vol. 29, pp. 1020-1030, 1998.
Sacharidou et al., "Endothelial lumen signaling complexes control 3D matrix-specific tubulogenesis through interdependent Cdc42- and Mti-MMP-mediated events," *Blood*, vol. 115, No. 25, pp. 5259-5269, 2010.
Sales et al., "Advancing vascular tissue engineering: the role of stem cell technology," *Trends Biotechnol*, vol. 23, No. 9, pp. 461-467, 2005.
Saunders et al., "Coregulation of vascular tube stabilization of endothelial cell TIMP-2 and pericyte TIMP-3," *J. Cell Biol.*, vol. 175, pp. 179-191, 2006.
Schatteman et al., "Blood-derived angioblasts accelerate blood-flow restoration in diabetic mice," *J. Clin. Invest.*, vol. 106, pp. 571-578, 2000.
Seliktar et al., "MMP-2 senstive, VEGF-bearing bioactive hydrogels for promotion of vascular healing," *J. Biomed. Mater. Res. A*, vol. 68, No. 4, pp. 704-716, 2004.
Shepherd et al., "Vascularization and engraftment of a human skin substitute using circulating progenitor cell-derived endothelial cells," *FASEB J.*, vol. 20, pp. 1739-1741, 2006.
Sheridan et al., "Bioabsorbable polymer scaffolds for tissue engineering capable of sustained growth factor delivery," *J Controlled Release*, vol. 64, No. 1-3, pp. 91-102, 2000.
Shu et al., "Synthesis and evaluation of injectable, in situ crosslinkable synthetic extracellular matrices for tissue engineering," *J. Biomed. Mater. Res. A*, vol. 79, pp. 902-912, 2006.
Sieminski et al., "Primary sequence of ionic self-assembling peptide gels affects endothelial cell adhesion and capillary morphogenesis," *Journal of Biomedical Materials Research*, vol. 87A, No. 2, pp. 494-504, 2008.
Sieminski et al., "The relative magnitudes of endothelial force generation and matrix stiffness modulate capillary morphogenesis in vitro," *Exp. Cell. Res.*, vol. 297, pp. 574-584, 2004.
Sieminski et al., "The Stiffness of Three-dimensional Ionic Self-assembling Peptide Gels Affects the Extent of Capillary-like Network Formation," *Cell Biochem. Biophys.*, vol. 49, pp. 73-83, 2007.
Silva et al., "Material-based deployment enhances efficacy of endothelial progenitor cells," *Proceedings of the National Academy of Sciences*, vol. 105, No. 38, pp. 14347-14352, Sep. 2008.
Srivastava et al.. "Potential of stem-cell-based therapies for heart disease," *Nature*, vol. 441, No. 7079, pp. 1097-1099, 2006.
Stephanou et al., "The rigidity in fibrin gels as a contributing factor to the dynamics of in vitro vascular cord formation," *Microvascular Research*, vol. 73, No. 3, pp. 182-190, 2007.
Stratman et al., "Endothelial cell lumen and vascular guidance tunnel formation requires MT1-MMP-dependent proteolysis in 3-dimensional collagen matrices," *Blood*, vol. 114, No. 2, pp. 237-247, 2009.
Sun et al., "Functional groups affect physical and biological properties of dextran-based hydrogels," *J Biomed Mater Res Part A*, vol. 93A, No. 3, pp. 1080-1090, 2010 (Published Online 2009).
Sun et al., "Functional neovascularization of biodegradable dextran hydrogels with multiple angiogenic growth factors," *Biomaterials*, vol. 32, p. 95, 2011.
Sun et al., "Vascular regeneration: engineering the stem cell microenvironment," *Regenerative Medicine*, vol. 3, No. 3, 435-47, 2009.
Sun et al., "VEGF-induced neuroprotection, neurogenesis, and angiogenesis after focal cerebral ischemia," *J. Clin. Invest.*, vol. 111, pp. 1843-1851, 2003.
Timmermans et al., "Endothelial progenitor cells: identity defined?" *J. Cell. Mol. Med.*, vol. 13, pp. 87-102, 2009.
Toole, "Hyaluronan in morphogenesis," *Semin. Cell. Dev. Biol.*, vol. 12, No. 2, pp. 79-87, 2001.
Toole, "Hyaluronan: From Extracellular Glue to Pericellular Cue," *Nat Rev Cancer*, vol. 4, No. 7, pp. 528-539, 2004.
Urbich et al., "Endothelial Progenitor Cells: Characterization and Role in Vascular Biology," *Circ Res*, vol. 95, No. 4, pp. 343-53, 2004.

(56) References Cited

OTHER PUBLICATIONS

Van Hinsbergh et al., "Pericellular Proteases in Angiogenesis and Vasculogenesis," *Arterioscler. Thromb. Vasc. Biol.*, vol. 26, pp. 716-728, 2006.
Vanderhooft et al., "Rheological Properties of Cross-Linked Hyaluronan-Gelatin hydrogels for Tissue Engineering," *Macromolecular Bioscience*, vol. 9, No. 1, pp. 20-28, 2009.
Written Opinion of the International Search Authority issued in Application No. PCT/US2011/042671 dated Feb. 17, 2012.
Written Opinion of the International Searching Authority issued in Application No. PCT/US2010/056268 dated Jul. 28, 2011.
Written Opinion of the International Searching Authority issued in Application No. PCT/US2012/034802 dated Nov. 26, 2012.
Xu et al., "Proteolytic exposure of a cryptic site within collagen type IV is required for angiogenesis and tumor growth in vivo," *The Journal of Cell Biology*, vol. 154, No. 5, pp. 1069-1080, 2001.
Yang et al., "The Design of Scaffolds for Use in Tissue Engineering," *Tissue Engineering*, vol. 7, No. 6, 679-89, 2001.
Yoder et al., "Redefining endothelial progenitor cells via clonal analysis and hematopoietic stem/progenitor cell principals," *Blood*, vol. 109, pp. 1801-1809, 2007.
Yoder, "Defining human endothelial progenitor cells," *Journal of Thrombosis and Haemostasis*, vol. 7, Suppl. 1, pp. 49-52, 2009.
Yoder, "Is Endothelium the Origin of Endothelial Progenitor Cells?" *Arterioscler. Thromb. Vasc. Biol.*, vol. 30, No. 6, pp. 1094-1103, May 2010.
Zaman et al., "Migration of tumor cells in 3D matrices is governed by matrix stiffness along with cell-matrix adhesion and proteolysis," *Proceedings of the National Academy of Sciences*, vol. 103, No. 29, pp. 10889-10894, 2006.
Zhang et al., "Properties and biocompatibility of chitosan films modified by blending with PEG," *Biomaterials*, vol. 23, p. 2641-2648, 2002.
Zhang et al., "Synthesis and Characterization of Biodegradable Hydrophobic-Hydrophilic Hydrogel Networks with a Controlled Swelling Property," *J. Polym. Sci. Polym. Chem.*, vol. 38, pp. 2392-2404, 2000.
Balakrishnan et al., *Biomaterials*, vol. 26, No. 32, pp. 6335-6342, 2005.
Boucard et al. *Biomaterials*, vol. 28, No. 24, pp. 3478-3488, 2007.
Cubison et al., *Burns*, vol. 32, No. 8, pp. 992-999, 2006.
Ehrbar et al., *Circ Res*, vol. 94, No. 8, pp. 1124-1132, 2004.
Extended European Search Report issued in European Application No. 10830680.4 dated Jun. 2, 2014. 9 printed pages.
Extended European Search Report issued in European Application No. 12786297.7 dated Jan. 12, 2015 8 printed pages.
Fagenholz et al., *J Burn Care Res*, vol. 28, No. 5, pp. 681-690, 2007.
Flamme et al., *Developmental Biology*, vol. 169, No. 2, pp. 699-712, 1995.
Fox et al., *British Journal of Surgery*, vol. 95, No. 2, pp. 244-251, 2008.
Gill et al., *Circ Res* vol., 88, No. 2, pp. 167-174, 2001.
Greenhalgh, The International Journal of Biochemistry & Cell Biology, vol. 30, No. 9, pp. 1019-1030, 1998.
Gurtner et al., *Nature*, vol. 453, No. 7193, pp. 314-321, 2008.
Hanjaya-Putra D, et al., *Blood*, vol. 118, No. 3, pp. 804-815, 2011.
Hao et al, "Angiogenic Effects of Sequential Release of VEGF-A 165 and PDGF-BB With Alginate Hydrogels After Myocardial Infarction." Cardiovascular Research. 2007; 75(1):178-185.
Haroon et al., The FASEB Journal, vol. 13, No. 13, pp. 1787-1795, 1999.
Inoue et al., *PLoS ONE*, vol. 3, No. 8, p. e3068, 2008.
Ismail et al., Cardiovasc Pathol, vol. 12, No. 2, pp. 82-90, 2003.
Ito et al., *Nature*, vol. 447, No. 7142, pp. 316-320.
Kim et al., *Biomaterials*, vol. 30, No. 22, pp. 3742-3748, 2009.
Kim et al., *J Invest Dermatol*, vol. 128, No. 7, pp. 1812-1820, 2008.
Kirker et al., Biomaterials, vol. 23, No. 17, pp. 3661-3671, 2002.
Kiyozumi et al., Burns, vol. 33, No. 5, pp. 642-648, 2007.
Kiyozumi et al., Journal of Biomedical Materials Research Part B: Applied Biomaterials, vol. 79B, No. 1, pp. 129-136, 2006.
Kloxin et al., Science, vol. 324, No. 5923, pp. 59-63, 2009.
Kurisawa et al., "Modulated degradation of dextran hydrogels grafted with poly(N-isopropylacrylamide-co-N,N-dimethylacrylamide) in response to temperature," Macromolecular Chemistry and physics, 199(11), pp. 2613-2618, 1998.
Lee et al., Mol Ther, vol. 15, No. 6, pp. 1189-1194, 2007.
Li et al., Microscopy Research and Technique, vol. 60, No. 1, 107-114, 2003.
Light et al., J Burn Care Rehabil, vol. 25, No. 1, pp. 33-44, 2004.
Liu et al., Biomaterials, vol. 30, No. 8, pp. 1453-1461, 2009.
Madsen et al., Biomacromolecules, vol. 9, No. 8, pp. 2265-2275, 2008.
Martin, Science, vol. 276, No. 5309, pp. 75-81, 1997.
Millius et al., Methods Mol. Biol., vol. 571, pp. 167-177, 2009.
Peichev et al., Blood, vol. 95, No. 3, pp. 952-958, 2000.
Puolakkainen et al., Journal of Surgical Research, vol. 58, No. 3, pp. 321-329, 1995.
Sase et al., J Cell Sci, vol. 122, No. 18, pp. 3303-3311, 2009.
Schulz et al., Annual Review of Medicine, vol. 51, No. 1, pp. 231-244, 2000.
Sen et al., J. Burn Care Res., vol. 31, No. 6, pp. 836-848, 2010.
Shepherd et al., Biomaterials, vol. 32, No. 1, pp. 258-267, 2011.
Shu et al., "Attachment and spreading of fibroblasts on an RGD peptide-modified injectable hyaluronan hydrogel," J. Biomed Materials Research, vol. 68, No. 2, 2004, pp. 365-375.
Sibal et al., Diabetologia, vol. 52, No. 8, pp. 1464-1473, 2009.
Singer et al., New England Journal of Medicine, vol. 341, No. 10, pp. 738-746, 1999.
Steed, Surgical Clinics of North America, vol. 77, No. 3, pp. 575-586, 1997.
Sun et al., "Dextran hydrogel scaffolds enhance angiogenic responses and promote complete skin regeneration during burn wound healing," PNAS, 2011, vol. 108, No. 52, pp. 20976-20981.
Tibbs, Radiotherapy and Oncology, vol. 42, No. 2, pp. 99-106, 1997.
Tredget, Journal of Trauma-Injury Infection and Critical Care, vol. 62, No. 6, pp. S69-S69, 2007.
Zhang et al., Arch Surg, vol. 145, No. 3, pp. 259-266, 2010.
Zhang et al., Wound Repair Regen., vol. 18, No. 2, pp. 193-201, 2010.
Office Action issued in U.S. Appl. No. 13/807,502 dated Mar. 11, 2016.
Office Action issued in U.S. Appl. No. 13/807,502 dated Mar. 27, 2015.
Office Action issued in U.S. Appl. No. 13/807,502 dated Nov. 17, 2016.
Office Action issued in U.S. Appl. No. 14/115,237 dated Jun. 24, 2015.
Office Action issued in U.S. Appl. No. 14/115,237 dated May 18, 2016.
Office Action issued in U.S. Appl. No. 14/115,237 dated Nov. 6, 2015.
Office Action issued in U.S. Appl. No. 14/115,237 dated Oct. 20, 2016.
Office Action issued in U.S. Appl. No. 14/553,442 dated Dec. 3, 2015.
Lee et al., Biomacromolecules Sep. 2008; 9:(9): 2315-2321.

* cited by examiner

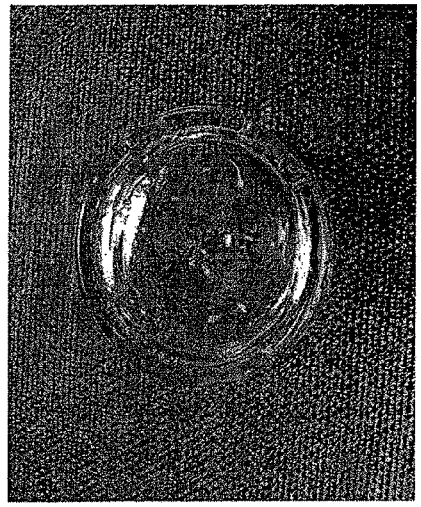
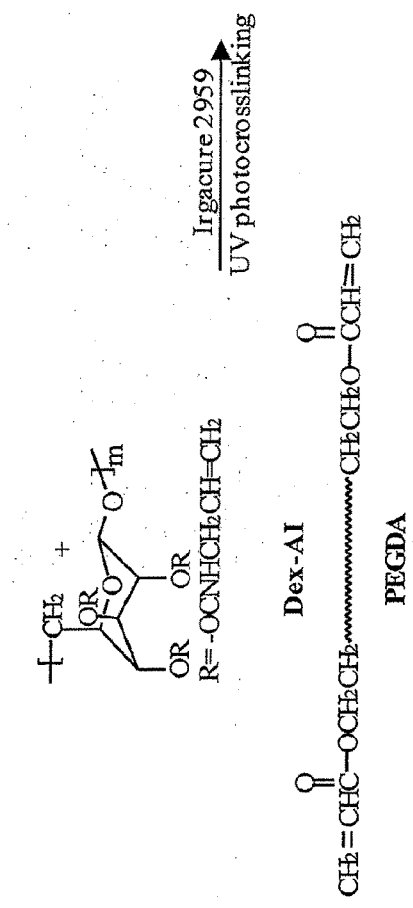
Figure 1A
| Hydrogel Sample | Dex/PEGDA ratios | | |
|---|---|---|---|
| | 20/80 | 40/60 | 60/40 |
| Dex-AI/PEGDA | 93.52% | 82.98% | 82.21% |
| Dex-AE/PEGDA | 80.58% | 72.58% | 70.76% |
| Dex-AM/PEGDA | 88.52% | 80.68% | 70.44% |
| Dex-AC/PEGDA | 90.38% | 84.22% | 77.38% |
Figure 1B

| | Weight loss, %(0.5U/mL) | | | | Weight loss, %(5U/mL) | | | |
|---|---|---|---|---|---|---|---|---|
| | Dex-AI /PEGDA | Dex-AE /PEGDA | Dex-AM /PEGDA | Dex-AC /PEGDA | Dex-AI /PEGDA | Dex-AE /PEGDA | Dex-AM /PEGDA | Dex-AC /PEGDA |
| 20/80 | 7.97±1.37 | 8.16±1.73 | 8.44±1.16 | 7.22±1.71 | 10.81±0.75 | 12.78±0.99 | 15.73±0.60 * | 13.42±1.16 |
| 40/60 | 11.41±1.46 | 14.46±1.26 | 14.01±1.28 | 8.26±1.06 | 14.06±0.68 | 17.09±0.61 | 20.71±2.33 ** | 14.01±0.72 |
| 60/40 | 14.01±1.33 | 18.49±0.81 * | 17.25±1.91 | 13.81±1.28 | 16.97±2.47 | 21.77±2.45 * | 22.06±1.64 * | 16.71±0.28 |

Figure 2B

| Hydrogel Sample | Dex/PEGDA ratios | | |
| --- | --- | --- | --- |
| | 20/80 | 40/60 | 60/40 |
| Dex-Al/PEGDA | 11.29±0.37 | 8.78±024 | 5.81±0.16 |
| Dex-AE/PEGDA | 10.38±0.28 | 4.91±0.09** | 1.31±0.05** |
| Dex-AM/PEGDA | 9.61±0.23 * | 7.29±0.28** | 2.07±0.11** |
| Dex-AC/PEGDA | 11.86±0.52 | 10.64±026** | 5.24±0.20* |

Figure 3B

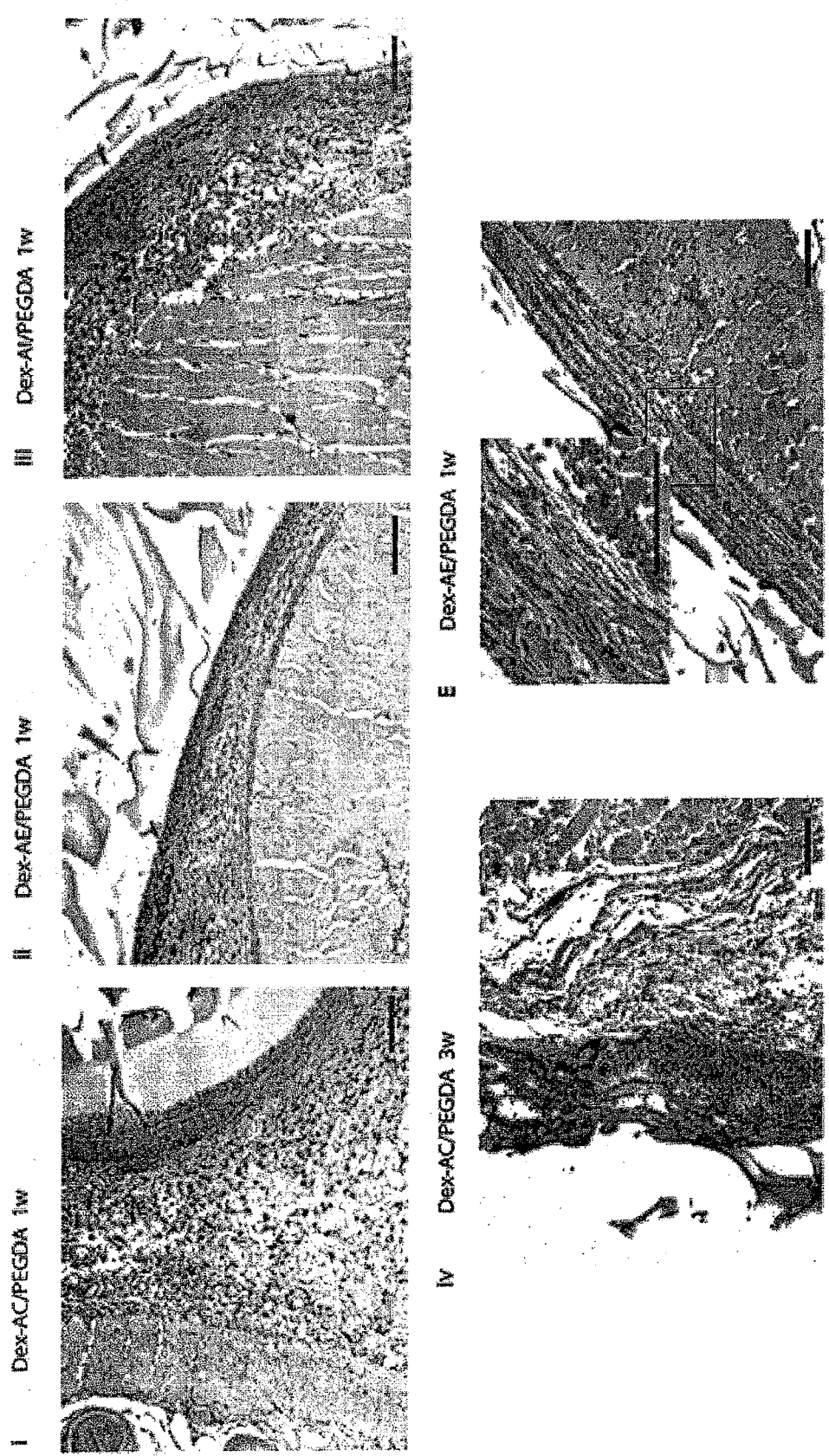
Figure 4D(i-iv) Figure 4E

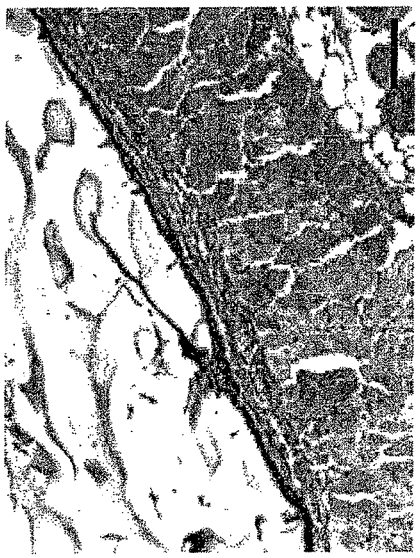
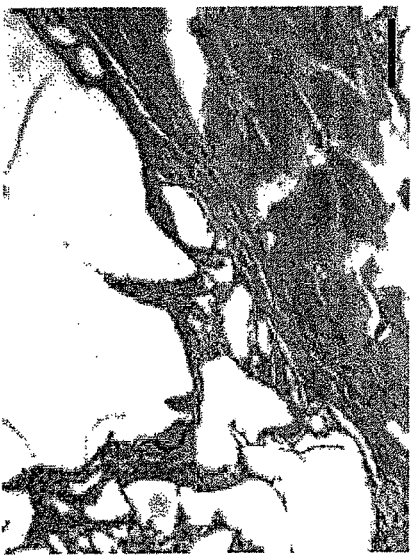
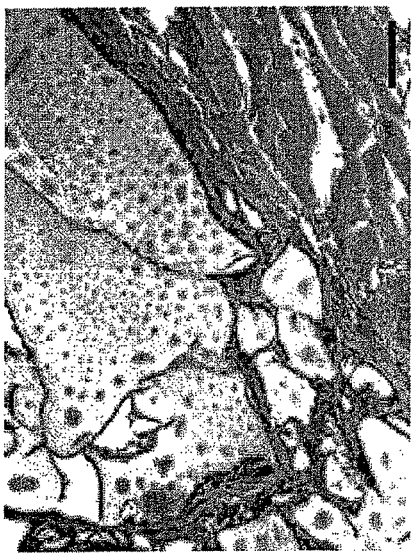
Figure 5C
Figure 5D(i)
Figure 5D(ii)
Figure 5E(i)
Figure 5E(ii)
Figure 5E(iii)

BIOCOMPATIBLE POLYSACCHARIDE-BASED HYDROGELS

CROSS-REFERENCE TO RELATED APPLICATION

This application claims priority to U.S. Provisional Application No. 61/138,335 filed Dec. 17, 2008, the entire contents of which are hereby incorporated by reference.

BACKGROUND

Field of the Invention

The present invention is related to with biocompatible polysaccharide-based hydrogels, components thereof and their use as delivery vehicles for proteins, oligonucleotides, pharmaceutical agents and cells.

Background of the Invention

Polymeric hydrogels have found a broad range of pharmaceutical and biomedical applications due to their three-dimensional structural and their functional similarity to natural tissues. A wide variety of hydrogels have been prepared, based on either physical or chemical crosslinking methods. The chemical crosslinking approach to designing biodegradable hydrogels is desirable because they are relatively easy to formulate by controlling experimental parameters, such as the type and concentration of crosslinking agents, initiator concentrations, and the ratios and concentrations of precursors.

Although many different types of polymeric hydrogels have been developed since the 1950s (Kopecek, J. *Nature* 2002, vol. 417, pp. 388-391), they all fall into one of two basic categories of polymer: natural or synthetic. Natural polymers have gained interest over the past few decades because of their biocompatibility and the presence of biologically recognizable groups to support cellular activities (Van Tomme et al. *Expert Rev. Med. Dev.* 2007, vol. 4, pp. 147-164). Among the natural polymers, dextran is a colloidal, hydrophilic, biocompatible, and nontoxic polysaccharide composed of linear $\alpha$-1,6-linked D-glucopyranose residues with a low fraction of $\alpha$-1,2, $\alpha$-1,3 and $\alpha$-1,4 linked side chains. Also, dextran can be biodegraded by dextranase, which exists in mammalian (including human) tissues. From a structural point of view, dextran has reactive hydroxyl groups (i.e. —OH) that can be modified to form hydrogels via crosslinking by photochemical and other means. As dextran is naturally resistant to protein adsorption and cell adhesion, modification of its polymer backbone allows development of a hydrogel with specific characteristics. Because of these properties, dextran and its hybrids have been extensively investigated as drug and/or gene carriers. For examples, dextran-based biomaterials have been employed in cell immobilization (Massia et al., *Biomaterials*, 2000, vol. 21, pp. 2253) and gene transfection (Azzam et al., *Macromol. Symp.*, 2003, vol. 195, p. 247) and as carriers for a variety of pharmaceutically active drugs (de Jong et al., *Macromolecules*, 2000, vol. 33, p. 3680; Kim et al., *J. Biomater. Appl.*, 2000, vol. 15, p. 23; Won et al., *Carbohydr. Polym.*, 1998, vol. 36, p. 327; Kim et al., *Arch. Pharma. Res.*, 2001, vol. 24, p. 69; Chu, C. C., in: *Biomaterials Handbook—Advanced Applications of Basic Sciences, and Bioengineering*, D. L. Wise (Ed.), p. 871. Marcel Dekker, New York, N.Y. (2003); Won et al., in: *Biomaterials & Engineering Handbook*, D. L. Wise (Ed.), p. 356. Marcel Dekker, New York, N.Y. (2000); Zhang et al., *J. Biomater. Appl.*, 2002, vol. 16, p. 305; Peppas et al., *Europ. J. Pharma.* *Biopharma.*, 2000, vol. 50, p. 27; Van Tomme et al., *Biomaterials*, 2006, vol. 27, p. 4141).

Many attempts have been made to engineer dextran-based polymers for various applications (Heinze et al., In *Polysaccharides Ii*, Springer-Verlag Berlin: Berlin, 2006; p. 199). Van Tomme et al. recently reviewed both chemically and physically crosslinked dextran-based hydrogels that were developed for protein release (Van Tomme et al. *Expert Rev. Med. Dev.* 2007, vol. 4, pp. 147-164). To generate chemically crosslinked dextran hydrogels, the major modification challenge is to introduce polymerizable bonds for efficient crosslinking. A common approach is to incorporate vinyl groups via different types of acrylates, thus enabling photocrosslinking. Such acrylates include glycidyl acrylate (Edman, et al., *I. J. Pharm. Sci.* 1980, vol. 69, pp. 838-842), glycidyl methacrylate (Vandijkwolthuis et al., *Macromolecules*, 1995, vol. 28, pp. 6317-6322), methacrylate (Kim et al., *J. Biomed. Mater. Res.*, 2000, vol. 53, pp. 258-266; Ferreira et al., *Biomaterials*, 2007, vol. 28, pp. 2706-2717), acrylate (Zhang et al., *J. Polym. Sci. Polym. Chem.*, 1999, vol. 37, pp. 4554-4569) and hydroxyethyl methacrylate (vanDijkWolthuis et al., *Macromolecules*, 1997, vol. 30, pp. 4639-4645; vanDijkWolthuis et al., *Polymer*, 1997, vol. 38, pp. 6235-6242). These hydrogels were proven to be efficient protein carriers. Chu et al. also developed maleic-anhydride- and allyl-isocyanate-(AI—) based dextran hydrogels (Kim et al., *J. Biomed. Mater. Res.*, 2000, vol. 53, pp. 258-266; Zhang et al., *J. Polym. Sci. Polym. Chem.*, 2000, vol. 38, pp. 2392-2404), which were shown to have tunable properties. Other than UV photocrosslinking, the Schiff reaction has also been employed to form crosslinks by oxidizing dextran rings into aldehyde groups (Maia et al., "Synthesis and characterization of new injectable and degradable dextran-based hydrogels," *Polymer*, 2005, vol. 46, pp. 9604-9614; Ito et al., *Biomaterials*, 2007, vol. 28, pp. 3418-3426).

One approach to preparing dextran-based hydrogels involves the use of a synthetic polymer precursor so that the resulting hydrogels can have both synthetic and naturally occurring polymers within a single entity. Among synthetic polymer precursors that coupled with dextran, polyethylene glycol) (PEG) is popular because it is a unique amphiphilic, biocompatible but non-biodegradable polymer, and has been explored for many biomedical applications. Though PEG is not biodegradable, lower molecular weight PEG can be readily excreted from the body via kidney and liver, thereby making it more suitable for drug delivery. In addition, PEG has also been employed to improve biocompatibility (Zhang et al., *Biomaterials*, 2002, vol. 23, p. 2641-2648; Chung et al., *Int. J. Biol. Macromol.*, 2003, vol. 32, p. 17), promote peptide immobilization (Hem et al., *J. Biomed. Mater. Res.*, 1998, vol. 39. p. 266; Wang et al., *J. Membr. Sci.*, 2002, vol. 195, p. 103), prolong protein drug circulating time (Koumenis et al., *Int. J. Pharma.*, 2000, vol. 198, p. 83; Greenwald et al., *Adv. Drug Deli. Rev.*, 2003, vol. 55, p. 217), increase bioactivity (Muslim et al., *Carbohydr. Polym.*, 2001, vol. 46. p. 323-330) and reduce immunogenicity (Hu et al., Int. *J. Biochem. Cell. Biol.*, 2002, vol. 34, p. 396-402).

SUMMARY

Embodiments of the invention include compositions of a polysaccharide with at least one monomer having at least one substituted hydroxyl group, wherein the polysaccharide includes a first substituted hydroxyl group of formula (I) and a second substituted hydroxyl group of formula (II), wherein formula (I) and formula (II) are different. The first and second substituted hydroxyl groups may be on the same or different monomers.

Formula (I) has the structure —$O_1$—X, where $O_1$ is the oxygen atom of the substituted hydroxyl group, and X is a crosslinkable moiety. Formula (II) has the structure Y—$(CR^2R^3)_n$—$CO_2H$, where Y is —$O_1$— or —$O_1C(O)$—, or —$O_1C(O)NR^1$— where $O_1$ is the oxygen atom of the substituted hydroxyl group, and $R^1$ is hydrogen or $C_1$-$C_4$ alkyl, n=1, 2, 3, or 4, $R^2$ and $R^3$ may be independently hydrogen, $C_1$-$C_4$ alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring.

Embodiments of the invention include a polysaccharide with at least one monomer having at least one substituted hydroxyl group, wherein the substituted hydroxyl group has the formula (III), and wherein the degree of substitution of formula (III) on the polysaccharide is less than about 0.2; wherein formula (III) is —$O_1$—$C(O)NR^7$—$CH_2CH$=$CH_2$ and $O_1$ is the oxygen atom of said substituted hydroxyl group and $R^7$ is hydrogen or $C_1$-$C_4$ alkyl. In some embodiments, $R^7$ is hydrogen In some embodiments, the polysaccharide further includes a second substituted hydroxyl group having the formula (IV), where formula (III) and formula (IV) are different, and the substituted hydroxyl group of formula (III) and formula (IV) may be on the same or different monomers. Formula (IV) is Y—$(CR^2R^3)_n$—Z, where Y is —$O_1$— or —$O_1C(O)$—, or —$O_1C(O)NR^1$—, $O_1$ is the oxygen atom of said substituted hydroxyl group, and $R^1$ is hydrogen or $C_1$-$C_4$ alkyl; n=1, 2, 3, or 4; Z is selected from the group consisting of —$CO_2H$ or $NR^4R^5$, where $R^4$ and $R^5$ are independently hydrogen or $C_1$-$C_4$ alkyl.

Other embodiments include a composition consisting essentially of the polysaccharides described above.

Other embodiments include compositions of the polysaccharide and a protein, oligonucleotide or pharmaceutical agent.

Other embodiments include compositions of the polysaccharide and a second crosslinkable material, such as poly (ethylene glycol) diacrylate. Other embodiments include compositions of the polysaccharide, poly(ethylene glycol) diacrylate, and a protein, oligonucleotide, or pharmaceutical agent.

Other embodiments include compositions of crosslinked polysaccharide. Further embodiments include compositions of a crosslinked blend of the polysaccharide and poly (ethylene glycol) diacrylate. Further embodiments include compositions of a crosslinked blend of polysaccharide, poly(ethylene glycol) diacrylate, and a protein, oligonucleotide, or pharmaceutical agent.

Embodiments of the invention include methods for delivering a protein, olignonucleotide or pharmaceutical agent to a subject by administering to the subject a composition of at least crosslinked polysaccharide and a protein, oligonucleotide or pharmaceutical agent.

Embodiments of the invention include hydrogel forming compositions having at least about 80% of a polysaccharide with at least one monomer having at least one substituted hydroxyl group, wherein the substituted hydroxyl group has the formula (III). Formula (III) has the structure —$O_1$—C (O)$NR^7$—$CH_2CH$=$CH_2$ where $O_1$ is the oxygen atom of the substituted hydroxyl group and $R^7$ is hydrogen or $C_1$-$C_4$ alkyl. The composition further includes up to about 20% of a second crosslinkable molecule. In some embodiments $R^7$ is H. In some embodiments, the second crosslinkable molecule is poly(ethylene glycol) diacrylate. In other embodiments, $R^7$ is H, and the second crosslinkable molecule is poly(ethylene glycol) diacrylate.

BRIEF DESCRIPTION OF THE DRAWINGS

FIG. 1 shows hydrogel preparation. FIG. 1A shows the chemical reaction (left) for forming an exemplary hydrogel (right). FIG. 1B shows a table of different hydrogels and their conversions.

FIG. 2 exemplifies swelling and degradation profiles of Dex/PEGDA hydrogels. FIG. 2B is a table of enzymatic biodegradation of Dex/PEGDA hydrogels in dextranase for 24 hours. Significance levels were set at: *$p<0.05$, $p<0.01$, and *$p<0.001$. Values shown are means±SD.

FIG. 3 exemplifies the mechanics and crosslinking density of Dex/PEGDA hydrogels. FIG. 3B is a table of crosslinking density ($\mu mol*cm^{-3}$) of Dex/PEGDA hydrogels. Significance levels were set at: *$p<0.05$, $p<0.01$, and *$p<0.001$. Values shown are means±SD.

FIG. 4 illustrates the biocompatibility of Dex/PEGDA hydrogels. In vitro—toxicity of Dex/PEGDA monomers on endothelial cells (ECs): FIG. 4D shows an enlarged inflammatory response observed 1 week after implantation of (i) Dex-AC/PEGDA compared to (ii) Dex-AE/PGDA and (iii) Dex-AI/PEGDA, and was found to decrease after 3-weeks (iv) as demonstrated by immunohistochemistry for macrophages (anti-ED-1). FIG. 4E is a representative image of dilated blood vessels (anti-CD31) observed in granulation layer as part of the healing response. Scale bars are 100 µm.

FIG. 5 shows $VEGF_{165}$ release from Dex/PEGDA hydrogels. FIG. 5C shows that transplantation of VEGF-releasing Dex- AE/PEGDA (40/60 ratio) elicited macrophage invasion as demonstrated by high magnification immunohistochemistry with anti-ED-1. FIG. 5D shows that little to no granulation tissue was observed after 7 weeks of transplantation of Dex-AE/PEGDA without VEGF (FIG. 5D(i)) and VEGF-releasing Dex-AE/PEGDA (FIG. 5D(ii)). FIG. 5E shows that after 7 weeks of transplantation, the majority of the VEGF-releasing Dex-AE/PEGDA hydrogel was fragmented (as demonstrated by H&E staining and high magnification, FIG. 5E(i)), engulfed with macrophages (as demonstrated by staining with anti-ED1 and high magnification, FIG. 5E(ii)), and engulfed with blood vessels (as demonstrated by staining with anti-CD31 and high magnification, (FIG. 5E(iii)). Scale bars are 100 μm.

FIG. 11 illustrates the Chemical characterization of (A) dextran; (B) Dex-AI; (C) Dex-AE; (D) Dex-AM; (E) Dex-AC.

DETAILED DESCRIPTION

Figure 2A:
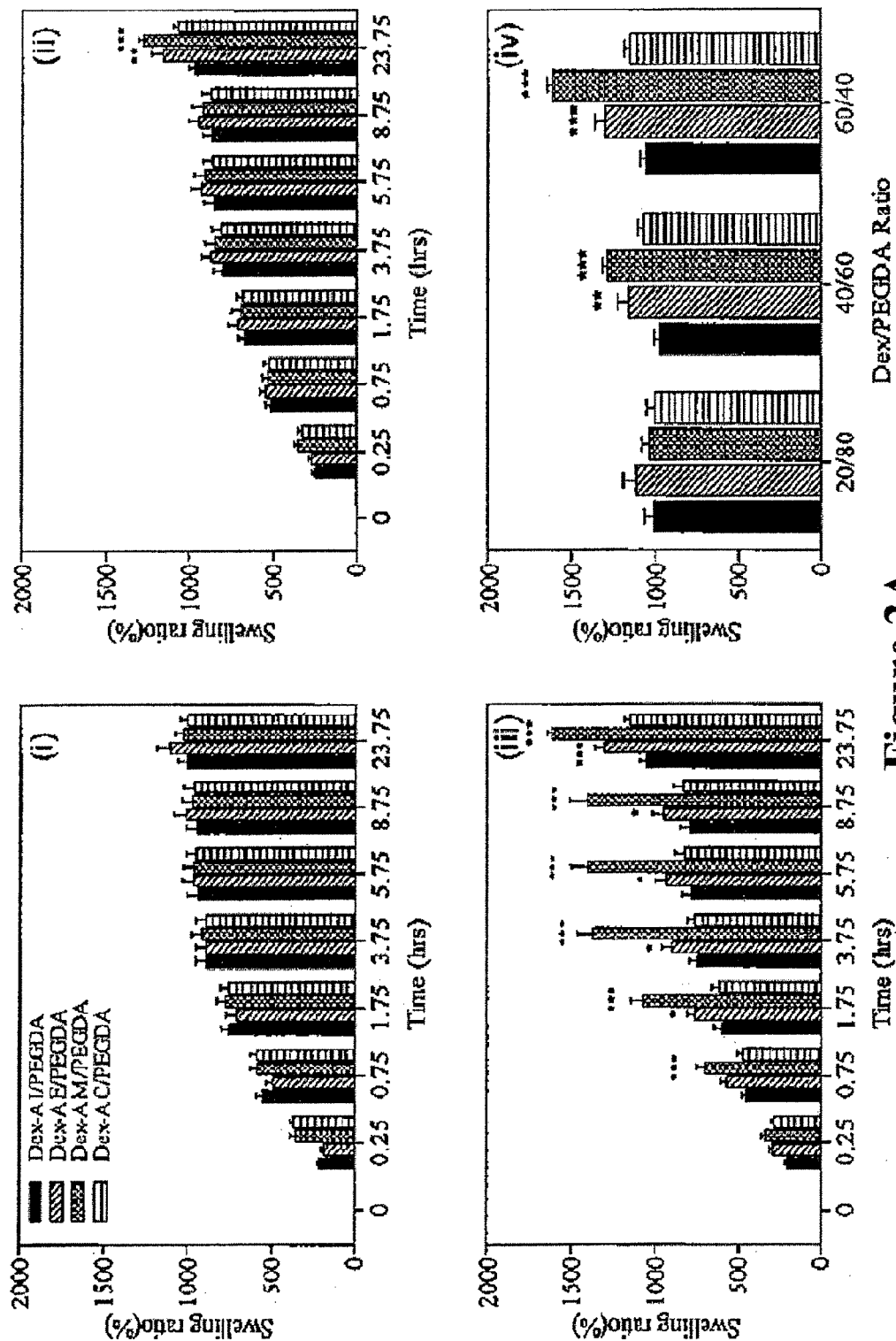
FIG. 2A graphically illustrates swelling volumes of dextran hydrogels over 24 hours, at three different Dex/PEGDA ratios: (i) 20/80; (ii) 40/60; (iii) 60/40; and (iv) the maximum swelling volumes of all hydrogels.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated. Headings used herein are provided for clarity and organizational purposes only, and are not intended to limit the scope of the invention.

DEFINITIONS

By "disease" is meant any condition or disorder that damages or interferes with the normal function of a cell, tissue, organ or subject.

By "effective amount" is meant the amount of an agent required to ameliorate the symptoms of a disease relative to an untreated subject. The effective amount of an active therapeutic agent for the treatment of a disease or injury varies depending upon the manner of administration, the age, body weight, and general health of the subject. Ultimately, the attending clinician will decide the appropriate amount and dosage regimen.

By "modifies" is meant alters. An agent that modifies a cell, substrate, or cellular environment produces a biochemical alteration in a component (e.g., polypeptide, nucleotide, or molecular component) of the cell, substrate, or cellular environment.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "subject" is meant an animal. In some embodiments, a subject may be a mammal, including, but not limited to, a human or non-human mammal, such as a bovine, equine, canine, ovine, or feline.

By "therapeutic delivery device" is meant any device that provides for the release of a therapeutic agent.

As used herein, the terms "treat," treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

The term "$C_1$-$C_4$ alkyl" as used herein means straight-chain, branched, or cyclic $C_1$-$C_4$ hydrocarbons which are completely saturated and hybrids thereof such as (cycloalkyl)alkyl. Examples of $C_1$-$C_6$ alkyl substituents include methyl (Me), ethyl (Et), propyl (including n-propyl (n-Pr, $^n$Pr), iso-propyl (i-Pr, $^i$Pr), and cyclopropyl (c-Pr, $^c$Pr)), butyl (including n-butyl (n-Bu, $^n$Bu), iso-butyl (i-Bu, $^i$Bu), sec-butyl (s-Bu, $^s$Bu), tert-butyl (t-Bu, $^t$Bu), or cyclobutyl (c-Bu, $^c$Bu)), and so forth.

The term "3-6 membered ring" as used herein means a saturated, unsaturated, or aromatic ring having 3 to 6 atoms in the ring and at least two carbon atoms in the ring. Non-carbon atoms may include nitrogen, oxygen, sulfur, phosphorous and silicon. Some embodiments have 1 or 2 heteroatoms in the ring. In some embodiments, the 3-6 membered ring may be a "$C_3$ to $C_6$ ring" having 3-6 carbon atoms in the ring. Examples of 3-6 membered rings include cyclopropane, cyclopropene, epoxides, aziridine, tioepoxides, cyclobutane, cyclobutene, cyclobutadiene, oxetane, azetidine, thietane, cyclopentane, cyclopentene, cyclopentadiene, pyrrolidine, pyrroline, pyrrole, imidazole, tetrahydrofuran, dihydrofuran, furan, oxazole, oxadiazole, thiazole, thiadiazole, tetrahydrothiophene, dihydrothiophene, thiophene, cyclohexane, cyclohexene, cyclohexadiene, benezene, piperazine, pyridine, tetrahydropyran, pyran, thiane, thiopyran, morpholine, diazines (including pyridazines, pyrimidines, and pyrazines), and triazine rings.

A polysaccharide having at least one substituted hydroxyl group can also be referred to as a "modified polysaccharide."

As used herein, "monomer," "saccharide monomer unit," "saccharide monomer," and the like are used to refer to a single saccharide unit of the polysaccharide. Saccharide monomers bearing a substituent are referred to herein as "modified monomers" or "modified saccharide monomers" or "modified saccharide monomer units."

Modified Polysaccharides and Compositions Thereof.

Carboxylate Containing Modified Polysaccharides

Embodiments of the invention include compositions of a polysaccharide with at least one monomer having at least one substituted hydroxyl group, wherein the polysaccharide includes a first substituted hydroxyl group of formula (I) and a second substituted hydroxyl group of formula (II), wherein formula (I) and formula (II) are different. The first and second substituted hydroxyl groups may be on the same or different monomers.

Formula (I) has the structure $-O_1-X$, where $O_1$ is the oxygen atom of the substituted hydroxyl group, and X is a crosslinkable moiety. Formula (II) has the structure $Y-(CR^2R^3)_n-CO_2H$, where Y is $-O_1-$ or $-O_1C(O)-$, or $-O_1C(O)NR^1-$ where $O_1$ is the oxygen atom of the substituted hydroxyl group, and $R^1$ is hydrogen or $C_1$-$C_4$ alkyl, n=1, 2, 3, or 4, $R^2$ and $R^3$ may be independently hydrogen, $C_1$-$C_4$ alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring.

In some embodiments, the modified polysaccharide has at least two substituents of formula (I). These substituents may be present on the same saccharide monomer unit, or the modified polysaccharide may have more than one modified saccharide monomer unit bearing a substituent of formula (I).

In some embodiments, the modified polysaccharide has at least two substituents of formula (II). These substituents may be present on the same saccharide monomer unit, or the modified polysaccharide may have more than one modified saccharide monomer unit bearing a substituent of formula (II).

As stated above $O_1$ is the oxygen atom of the substituted hydroxyl group of a substituted saccharide monomer unit. A substituted hydroxyl group may have the structure of formula (I) or formula (II), so long as both formula (I) and formula (II) are present in the polysaccharide. For instance, one saccharide monomer of the polysaccharide may have a substituent of formula (I), while a separate monomer has a substituent of formula (II). In other cases, the substituent of formula (I) and formula (II) may be present on the same monomer. Multiple monomers of the polysaccharide may have substituents of formula (I) or formula (II). Formula (I) and formula (II) are different. In other words, formula (I) and formula (II) do not describe the same structure, and both must be present on the polysaccharide.

As used herein, a crosslinkable moiety is a chemical substituent capable of reacting with another chemical substituent, forming a covalent bond or crosslink between two moieties. In general, the crosslinking reaction occurs between different molecules, forming a crosslink between two different polysaccharide molecules, or between a polysaccharide molecule and another molecule, though crosslinks may also occur within a single polysaccharide. As will be readily understood in the art, two polysaccharides or different portions of a single polysaccharide, each of which contains at least one crosslinkable moiety may be reacted with a non-saccharide molecule or polymer having two or more crosslinkable moieties. In the resultant structure, two polysaccharides or different portions of the same polysaccharide are joined by a non-saccharide linking moiety, for example, a poly(ethylene glycol). When crosslinked, a polysaccharide may have multiple crosslinks to itself and/or multiple other molecules.

In some embodiments, the crosslinkable moiety is a double bond containing moiety. A double bond containing moiety is a substituent having at least one double bond in the structure, the double bond may be part of, for example, a vinyl, allyl, acrylate, methacrylate, or alkyl acrylate structure. In some embodiments, the crosslinkable moiety is derived from glycidyl acrylate, glycidyl methacrylate, methacrylate, acrylate, hydroxyethyl methacrylate, maleic anhydride, or allyl isocyanate. As used herein, "derived from" means that the crosslinkable moiety is the product of a reaction between the hydroxyl group and, e.g., glycidyl acrylate or allyl isocyanate. In certain embodiments, the crosslinkable moiety is an allyl carbamate or allyl urethane. In other embodiments, the substituent of formula (I) has the structure $-O_1-C(O)-NR^8-CH_2CH=CH_2$ where $R^8$ is hydrogen or $C_1$-$C_4$ alkyl. In some embodiments, the crosslinkable moiety is derived from allyl isocyanate. In other words, the substituent of formula (I) has the structure $-O_1-C(O)-NH-CH_2CH=CH_2$.

Polysaccharides with Low Degree of Substitution

Embodiments of the invention include a polysaccharide with at least one monomer having at least one substituted hydroxyl group, wherein the substituted hydroxyl group has the formula (III), and wherein the degree of substitution of formula (III) on the polysaccharide is less than about 0.2; wherein formula (III) is $-O_1-C(O)NR^7-CH_2CH=CH_2$ and $O_1$ is the oxygen atom of said substituted hydroxyl group and $R^7$ is hydrogen or $C_1$-$C_4$ alkyl. "Degree of substitution" (DS) is defined as the average number of substituted hydroxyl groups per saccharide monomer. A degree of substitution less than about 0.2 means that the number of substituted hydroxyl groups having the structure of formula (III) in the polysaccharide, divided by the total number of monomers in the polysaccharide is less than about 0.2. The degree of substitution can be calculated from the NMR spectrum. For example, the ratio of the sum of the normalized, integrated intensities of the hydroxyl group peaks to the normalized, integrated intensities of the anomeric proton peak is subtracted from the number of unsubstituted hydroxyl groups in an unmodified monomer unit to determine the degree of substitution. For dextran polysaccharides, for example, each dextran monomer unit has three hydroxyl groups. If, for example, the sum of the integrated intensities of the hydroxyl peaks was 11, and the integrated intensity of the anomeric proton was 4, the ratio would be 2.75. This value (2.75) is subtracted from the total number of hydroxyls (3), to calculate the degree of substitution (3−2.75=0.25). This also corresponds to an average of one substituted hydroxyl group for every 4 monomer units. In some embodiments, the degree of substitution may be between about 0.01 and about 0.2. In other embodiments, the degree of substitution is less than about 0.18, less than about 0.15, less than about 0.13, or less than about 0.10. In some embodiments, the degree of substitution is greater than about 0.01, greater than about 0.03, greater than about 0.05, or greater than about 0.07. Embodiments of the invention may have any combination of maximum and minimum previously specified.

In some embodiments, $R^7$ is hydrogen.

In some embodiments, the polysaccharide further includes a second substituted hydroxyl group having the formula (IV), where formula (III) and formula (IV) are different, and the substituted hydroxyl group of formula (III) and formula (IV) may be on the same or different monomers. Formula (IV) is $Y-(CR^2R^3)_n-Z$, where Y is $-O_1-$ or $-O_1C(O)-$, or $-O_1C(O)NR^1-$, $O_1$ is the oxygen atom of said substituted hydroxyl group, and $R^1$ is hydrogen or $C_1$-$C_4$ alkyl; n=1, 2, 3, or 4; Z is selected from the group consisting of $-CO_2H$ or $NR^4R^5$, where W and $R^5$ are independently hydrogen or $C_1$-$C_4$ alkyl.

In some embodiments, Z is $NR^4R^5$. In some embodiments, formula (IV) is $-O_1-(CH_2CH_2)-NH_2$.

It is advantageous to prepare hydrogels that utilize high percentages (e.g., greater than 80%) of polysaccharides. For example, such hydrogels exhibit improved biocompatibility and biodegradation. However, conventional polysaccharides, when used to with crosslinking agents, often do not have favorable gel forming characteristics. Polysaccharides with low degrees of substitution of a crosslinking moiety on a hydroxyl group have been found to form hydrogels with high polysaccharide content. Accordingly, in some embodiments, the present invention includes polysaccharides that are capable of forming a hydrogel having at least about 80% of a polysaccharide, when the polysaccharide has at least one monomer having at least one substituted hydroxyl group, wherein the substituted hydroxyl group has the formula (III). No particular maximum or minimum degree of substitution is required, so long as a solid gel can be formed. Hydrogels and hydrogel forming compositions according to this embodiments are described below.

Compositions

Some embodiments include compositions consisting essentially of the modified polysaccharide. The modified polysaccharide in the composition may be isolated or purified, meaning that the modified polysaccharide has been at least partially separated from the reagents used to prepare the modified polysaccharide. The modified polysaccharide may be uncrosslinked, or may be crosslinked.

Other embodiments of the invention include the modified polysaccharide described above by itself, or as part of a mixture with other materials.

In other embodiments, the at least one hydroxyl-substituted saccharide monomer is a glucopyranose monomer. The glucopyranose monomer may be substituted at any available free hydroxyl group, or may be substituted on more than one available free hydroxyl group. The glucopyranose monomer may be incorporated into the polysaccharide in any suitable orientation, for example, via a 1,2-, 1,3-, 1,4-, 1,6-, or other linkage.

In some embodiments, the polysaccharide is dextran. In some embodiments, the dextran has an average molecular weight of at least about 20,000. The dextran may have an average molecular weight of at least about 30,000, at least about 40,000, at least about 50,000, or at least about 60,000. The dextran may have an average molecular weight less than about 200,000, less than about 150,000, or less than about 100,000. The dextran may have a molecular weight between any two endpoints. The molecular weight may be number average or weight average. For instance, the dextran molecule may have an average molecular weight between about 20,000 and about 200,000, between about 20,000 and about 100,000 or between about 40,000 and about 70,000.

In some embodiments, the composition further comprises a protein, oligonucleotide or pharmaceutical agent. In general, any protein, oligonucleotide or pharmaceutical agent which may be delivered by a hydrogel may be delivered by the compositions of the present invention. Examples of proteins that may be delivered by hydrogels include bovine serum albumin (BSA) or ovalbumin. In some embodiments, the protein is a therapeutic protein, such as insulin or immunoglobulins (such as IgG). In some embodiments, the therapeutic protein is a growth factor. Examples of growth factors include vascular endothelial growth factor (VEGF), insulin growth factor (IGF), keratinocyte growth factor (KGF), stromal-cell derived factor (SDF), and angiopoetin (Ang). In some embodiments, the oligonucleotide is an antisense oligonucleotide.

In some embodiment, the composition further comprises poly(ethylene glycol) diacrylate. In other embodiments, the poly(ethylene glycol) diacrylate has a molecular weight of at least about 2000, at least about 4000, at least about 6000, at least about 8000, or at least about 10,000. In some embodiments, the poly(ethylene glycol) diacrylate has a molecular weight less than about 50,000, less than about 20,000, or less than about 15,000. The poly(ethylene glycol) diacrylate may have an a molecular weight of between any two previously disclosed endpoints. The molecular weight may be number average or weight average. In general, larger poly(ethylene glycol) polymers are cleared more slowly from the body by the kidneys. Larger poly(ethylene glycol) may result in hydrogels with a looser structure, larger pore size, and higher swelling. Persons skilled in the art can use routine experimentation to determine and select a poly(ethylene glycol) or poly(ethylene glycol) diacrylate to provide desired physical properties for a hydrogel according to the invention.

In some embodiments, the weight ratio between the polysaccharide and poly(ethylene glycol) diacrylate is between about 10:1 and about 1:10. In other embodiments, the weight ratio of the polysaccharide and poly(ethylene glycol) diacrylate is between about 80:20 and 20:80. In other embodiments, the weight of the polysaccharide and poly(ethylene glycol) diacrylate is between about 70:30 and 30:70. In other embodiments, the weight ratio between the polysaccharide and poly(ethylene glycol) diacrylate is between about 60:40 and 40:60. In some embodiments, the weight ratio between the polysaccharide and poly(ethylene glycol) diacrylate is about 20:80, about 40:60 or about 60:40.

In embodiments having a polysaccharide having a low degree of substitution of formula (III), described above, the composition may have a percentage (by weight) of modified polysaccharide of greater than about 80%. In other embodiments, the percentage (by weight) of modified polysaccharide may be greater than about 40%, greater than about 50%, greater than about 60% or greater than about 70%.

Crosslinked Compositions

In some embodiments the composition includes a crosslinked modified polysaccharide described above. The composition may be crosslinked between polysaccharide molecules, or between polysaccharide molecules and one or more other crosslinkable molecules. Other embodiments include compositions of a crosslinked blend of polysaccharide and a second crosslinkable molecule. In some embodiments, the second crosslinkable molecule is a polymer. As used herein, a "crosslinkable" molecule or polymer is a material bearing at least two reactive groups capable of forming a covalent bond or crosslink with the crosslinkable moiety of the polysaccharide. Examples of crosslinkable molecules include, for example, vinyl groups, acrylate groups and, methacrylate groups. Polymers having at least two crosslinkable groups are useable, such as, poly(alkyleneglycol) diacrylate, poly(alkyleneglycol) dimethacrylate. Specific examples include poly(ethylene glycol) diacrylate. Other polymers, both degradable and nondegradable may be used. Examples include hyaluronic acid, chitosan or poly (ester amide) polymers having crosslinkable moieties. Crosslinkable moieties other than double bonds may also be used, such as thiol containing polymers. Thiol containing polymers may crosslink with double bond crosslinking moieties on the polysaccharide, or thiol-containing moieties on the polysaccharide. This chemistry may be useful for non-photocrosslinking where UV irradiation is not desirable.

As described above, when a second crosslinkable molecule is used, there is a non-saccharide linking moiety between the crosslinked polysaccharides. For example, when the second crosslinkable molecule is poly(ethylene glycol) diacrylate, the linking moiety is a polyethyelene glycol. In some embodiments the crosslinked composition is a hydrogel. In other embodiments, the crosslinked composition is a hydrogel comprising a blend of polysaccharide and poly(ethylene glycol) diacrylate.

Other Hydrogels and Hydrogel Forming Compositions

Embodiments of the invention include hydrogel forming compositions having at least about 80% of a polysaccharide with at least one monomer having at least one substituted hydroxyl group, wherein the substituted hydroxyl group has the formula (III). Formula (III) has the structure $-O_1-C(O)NR^7-CH_2CH=CH_2$ (III) where $O_1$ is the oxygen atom of the substituted hydroxyl group and $R^7$ is hydrogen or $C_1$-$C_4$ alkyl. The composition further includes up to about 20% of a second crosslinkable molecule. In some embodiments $R^7$ is H. In some embodiments, the second crosslinkable molecule is poly(ethylene glycol) diacrylate. In other embodiments, $R^7$ is H, and the second crosslinkable molecule is poly(ethylene glycol) diacrylate.

A "hydrogel forming composition" as used herein means a composition capable of forming a solid hydrogel when photocrosslinked, rather than a fluid-like gel. Persons skilled in the art will generally be able to distinguish a solid hydrogel from a fluid-like hydrogel. For instance, a "solid hydrogel" is capable of maintaining its shape after photocrosslinking, or has sufficient structure that mechanical properties, such as the modulus may be measured. However, by way of example, and not limitation, a solid hydrogel may be considered a hydrogel having an increase in mechanical strength. Alternatively, a solid hydrogel may be a gel with a modulus greater than about 200 Pa, greater than about 500 Pa, greater than about 700 Pa, or greater than about 1000 Pa. In some embodiments, the degree of substitution of formula (III) is about 0.2 or less.

As mentioned above, hydrogels according to the invention can be formed by crosslinking through use of, for example, chemical and photochemical means. Photochemical crosslinking can offer some advantages including reduction in the exposure to chemical initiators or other reagents, and greater control over degree of crosslinking by having direct control over exposure to light. In many cases, it is still advantageous to reduce the exposure time to UV radiation. For this reason, certain embodiments include hydrogels and hydrogel forming compositions that form solid hydrogels in a particular period of time. For instance, the compositions may form solid hydrogels in less than about 1 hour, less than about 45 minutes, less than about 30 minutes, or less than about 20 minutes using photoirradiation at 365 nm with a lamp power of about 100 W.

Other embodiments include a hydrogel forming composition having a second substituted hydroxyl group having the formula (IV), where formula (III) and formula (IV) are different, and the substituted hydroxyl group of formula (III) and formula (IV) may be on the same or different monomers. As discussed above, formula (IV) has the structure $Y-(CR^2R^3)_n-Z$ where Y is $-O_r-$ or $-O_1C(O)-$, or $-O_1C(O)NR^1-$, $O_1$ is the oxygen atom of said substituted hydroxyl group, and $R^1$ is hydrogen or $C_1$-$C_4$ alkyl; n=1, 2, 3, or 4; Z is selected from the group consisting of $-CO_2H$ or $NR^4R^5$, where $R^4$ and $R^5$ are independently hydrogen or $C_1$-$C_4$ alkyl. $R^2$ and $R^3$ are independently hydrogen, $C_1$-$C_4$ alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring. In some embodiments, Z is $NR^4R^5$. In other embodiments, formula (IV) is $-O_1-(CH_2CH_2)-NH_2$.

Other embodiments include photocrosslinked composition of the hydrogel forming compositions described above.

Other embodiments include a hydrogel having at least about 80% of at least one polysaccharide portion and up to about 20% poly(ethylene glycol) diacrylate portions, where the polysaccharide portion is derived from a polysaccharide with at least one monomer having at least one substituted hydroxyl group, and the substituted hydroxyl group has the formula (III). The hydrogel is formed by photocrosslinking. As discussed above, formula (III) has the structure $-O_1-C(O)NR^7-CH_2CH=CH_2$ where $O_1$ is the oxygen atom of said substituted hydroxyl group and $R^7$ is hydrogen or $C_1$-$C_4$ alkyl.

Other embodiments include a hydrogel having at least about 80% of at least one polysaccharide portion and up to about 20% poly(ethylene glycol) diacrylate portions, as discussed above, where the polysaccharide has a second substituted hydroxyl group having the formula (IV), where formula (III) and formula (IV) are different, and the substituted hydroxyl group of formula (III) and formula (IV) may be on the same or different monomers. As discussed above, formula (IV) has the structure $Y-(CR^2R^3)_n-Z$ where Y is $-O_1-$ or $-O_1C(O)-$, or $-O_1C(O)NR^1-$, $O_1$ is the oxygen atom of said substituted hydroxyl group, and $R^1$ is hydrogen or $C_1$-$C_4$ alkyl; n=1, 2, 3, or 4; Z is selected from the group consisting of $-CO_2H$ or $NR^4R^5$, where $R^4$ and $R^5$ are independently hydrogen or $C_1$-$C_4$ alkyl. $R^2$ and $R^3$ are independently hydrogen, $C_1$-$C_4$ alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring. In some embodiments, Z is $NR^4R^5$. In other embodiments, formula (IV) is $-O_1-(CH_2CH_2)-NH_2$.

In general, biocompatible hydrogels having a higher concentration of polysaccharide are advantageous, because a greater portion of the hydrogel can be metabolically degraded. This results in greater control of the amount of added components released from the hydrogel matrix, because more of the matrix can be metabolized in vivo.

In some embodiments, the hydrogel forming composition may produce a hydrogel with a swelling ratio of greater than about 1200% The swelling ratio may be determined gravimetrically by immersing a dry hydrogel sample of known weight in distilled water, and measuring the increase in weight until the weight no longer changes. The swelling ratio can then be calculated according to formula (1)

$$\text{Swelling ratio} = ((W_{s,t} - W_d)/W_d) \times 100\% \quad (1)$$

where $W_d$ is the weight of dry hydrogels, and $W_{s,t}$ is the weight of swollen hydrogels at time t. The hydrogels were assumed to reach a state of swelling equilibrium when there was no difference in swelling ratio between two adjacent intervals.

In other embodiments, the composition may produce a hydrogel having a swelling ratio of greater than about 1500%, greater than about 1700% or greater than about 1900%. The hydrogels of the present invention may have a swelling ratio of greater than about 1200%, greater than about 1500, greater than about 1700%, or greater than about 1900%. In general, an increased swelling ratio results in an increased release rate of any added components such as proteins.

Added Components

In some embodiments, the crosslinked composition or hydrogels discussed previously further include a protein, oligonucleotide, or pharmaceutical agent. In some embodiments, the crosslinked composition comprises a protein, oligonucleotide, or pharmaceutical agent that is released from the composition over time, when present in an environment, for example an aqueous environment, having a lower concentration of the protein, oligonucleotide, or pharmaceutical agent. "Released from the composition" as used herein, means that the concentration of protein oligonucleotide, or pharmaceutical agent in the crosslinked composition decreases. The aqueous environment may be, for instance, a buffer, such as phosphate buffered saline (PBS) or other buffer. The buffered solution may also include dextranase enzyme or dextranase enzyme may be added. The "aqueous environment" also includes situations where the crosslinked composition is administered to a subject for the purpose of delivering a protein, oligonucleotide, or pharmaceutical agent to the subject. The environment into which the protein, oligonucleotide, or pharmaceutical agent is released can be blood, lymph, tissue, for example an organ tissue, gastric juices, or other environment.

In some embodiments, when a crosslinked composition of modified polysaccharide, poly(ethylene glycol) diacrylate and protein is incubated at 37° C. in phosphate buffered saline (PBS), less than 10% of the protein (by weight) is released from the crosslinked composition in the first 24 hours.

Methods

Hydrogels according to the invention can be used as tissue engineering scaffolds, cosmetics, wound care and other purposes. Exemplary embodiments of the invention include methods for delivering a protein, oligonucleotide or pharmaceutical agent comprising administering to a subject a crosslinked composition having at least a modified polysaccharide described above, and a protein, oligonucleotide or pharmaceutical agent to be delivered, wherein the protein, oligonucleotide or pharmaceutical agent is released from the crosslinked composition over time after administration. Some embodiments include methods for delivering proteins to a subject comprising administering to said subject a crosslinked composition having at least a polysaccharide described above and said protein. In some embodiments, the protein is a therapeutic protein.

Other embodiments of the invention include methods of increasing vascular regeneration comprising administering a composition described above. In some embodiments, the composition further includes a protein that increases vascular regeneration. In some embodiments, the protein is vascular endothelial growth factor (VEGF). Other proteins that increase vascular regeneration include insulin growth factor (IGF), stromal-cell derived factor (SDF), and angiopoetin (Ang), such as angiopoetin-1 (Ang-1).

In some instances, the hydrogel may provoke tissue response and increase or promote vascular regeneration without any additional protein.

When a protein, such as VEGF, that increases vascular growth is administered in a composition described above, the protein is released over time from the composition, causing increased vascular growth. Compositions of this sort may be used, for example, for the treatment of wounds or burns by applying the composition to the surface of the body. The composition may also be administered subcutaneously (i.e. below the skin) to increase vascular growth or regeneration. In other cases, the composition may be implanted at a specific location in the body, inducing vascular growth for the treatment of, for example, ischemias.

The crosslinked compositions and hydrogels described above may be administered by any available route for administering hydrogels to a subject. The compositions may be formulated with at least one pharmaceutically acceptable carrier depending on the method of administration. The compositions may be administered, for example, orally, parenterally, subcutaneously or topically, depending on the material to be delivered to the subject and the targeted tissue.

In some embodiments, the composition may be administered to a subject as an uncrosslinked composition, followed by photochemical crosslinking. In this way, the hydrogels may be molded to a particular shape, based on the location of administration, for example on a targeted organ. The uncrosslinked composition may be crosslinked externally or internally.

In some embodiments, the composition is crosslinked prior to administration. The crosslinked composition may be formed in a particular shape, for example as ovoid, sphere, disc, sheet or other structure. Crosslinked compositions may be administered internally or externally.

After administration, the protein, oligonucleotide or pharmaceutical agent is released from the crosslinked composition. The rate of release may be steady, i.e. a certain percentage, by weight, over a period of time. In other cases, a portion of the protein, oligonucleotide or pharmaceutical agent may be released at an increasing initial rate after administration, followed by a steady-state release. In other cases, the rate of release may decrease over time after administration.

In some embodiments, a certain percentage, by weight, of the protein, oligonucleotide, or pharmaceutical agent is released in a given period of time. Embodiments of the invention include methods for sustained release of a protein, oligonucleotide, or pharmaceutical agent by administering compositions described previously. In some embodiments, the protein, oligonucleotide, or pharmaceutical agent may be released over about 24 hours or more, about 48 hours or more, or about 72 hours or more.

For example, less than about 10%, by weight, of the protein, oligonucleotide or pharmaceutical agent may be released from the crosslinked composition in the first 24 hours. In different embodiments, less than about 30%, less than about 20%, less than about 10%, or less than about 5% by weight may be released over the first 12 hours, 24 hours, or 48 hours. Zero order release, where the additional component is released at a steady state is advantageous in certain circumstances. In other cases, a temporal, stimuli responsive release is desirable. The release profile may be selected based on the desired application.

The release profile may be modified by changing the substituent(s) on the polysaccharide, or by varying the ratio between modified polysaccharide and second crosslinkable compound in the crosslinked composition, by varying the sizes of the polysaccharide or second crosslinking compound, or by changing the degree of substitution on the polysaccharide. Other factors such as pH may also influence the rate of release. The release profile is also influenced by the degradation rate of the crosslinked composition, which will vary from subject to subject.

There are two basic release mechanisms, diffusion, and degradation, and combinations of the two may occur. In the diffusion mechanism, a higher degree of swelling will make the diffusion faster, thus causing faster release. A hydrogel with loose structures (i.e. less crosslinked) will also make diffusion faster. A higher degree of crosslinking cause dense structures, with less diffusion. The degradation rate is dominated by the degradation polymers. For the same hydrogel system (e.g. Dex-AE/PEGDA), more degradable polymer component means faster degradation, and therefore faster release. Accordingly, persons skilled in the art will be able to modify the hydrogel structure and the polymer to achieve a desired release profile.

Preparation

The polysaccharides described above may be prepared according to methods known in the art. For instance, the unsubstituted polysaccharide bearing a reactive hydroxyl group may be reacted with a reagent bearing a crosslinkable moiety to produce the structure of formula (I). The reagent may react with the free hydroxyl group directly, or the reagent or hydroxyl group may be activated to react with the reagent. Examples of substituents which may react directly with the free hydroxyl group to produce the structure of formula (I) include epoxides, such as glycidyl acrylate and glycidyl methacrylate; anhydrides, such as maleic anhydride, acrylic anhydride, or methacrylic anhydride; isocyanates, such as allyl isocyanate; acyl halides, such as acryloyl chloride, or methacryloyl chloride; alkyl halides such as allyl bromide, or 2-chloroethyl acrylate, or 2-chloroethyl methacrylate. Other reagents may have activatable groups, i.e. moieties that can be activated to react with the free hydroxyl group. Activateable groups include carboxylic acids, hydroxides or amines to form, for example, esters, ethers, carbonates, or carbamate (urethane) linkages.

The polysaccharide may be reacted with a reagent bearing a free carboxylic acid or carboxylate group to form the substituent having formula (II). For example, substituents having an ether linkage to the saccharide may be prepared from haloalkyl carboxylic acids, such as chloroacetic acid, 2-bromopropionic acid, 4-bromobutyric acid, or 5-chlorovaleric acid. Substituents having an ester linkage may be prepared, for example by reaction with a cyclic anhydride, such as maleic anhydride or succinic anhydride, or other activated carboxylate reagent such as a mono-activated di-acid. Substituents having a carbamate linkage may be prepared, for example, from carboxylic acid bearing isocyanate reagents, such as glycyl isocyante, other amino acid isocyanate, or from activated amines.

A hydroxyl group on the polysaccharide may be substituted to form the substituent of formula (I) first, followed by substituting another hydroxyl group to form the substituent of formula (II), or vice versa. In some cases, both substituents may be formed in the same reaction by adding both reagents to the unsubstituted polysaccharide.

Polysaccharide having substituted hydroxyl groups with the structure of formula (III) with a low degree of substitution may be prepared, for example, by reacting a polysaccharide with allylisocyanate in the presence of an activator, such as dibutyltin dilaurate (DBTDL). The degree of substitution is controlled by reducing the mole ratio of allylisocyanate to polysaccharide to produce the desired degree of substitution.

The modified polysaccharide having the substituent of formula (III) may then be reacted with a reagent to form a substituent of formula (IV) using reagents discussed previously. Substituents of formula (IV) where Z is $NR^5R^6$ may be prepared, for example, by reacting the modified polysaccharide with an amine bearing reagent similar to those described previously having a carboxylic acid. For example, the polysaccharide may be reacted with 2-bromoethylamine hydrobromide to form the substituent having the formula $-O_1-(CH_2CH_2)-NH_2$. Alternatively, a polysaccharide may be reacted with a reagent to form a substituent of formula (IV), and then reacted with a reagent to form a hydroxyl group with the structure of formula (III).

The polysaccharide may be purified, for example, by precipitation, or by chromatography, such as size exclusion chromatography.

Crosslinked compositions may be prepared by crosslinking the modified polysaccharide using any suitable chemistry, based on the crosslinking moiety. In some embodiments, where the crosslinking moiety comprises a double bond, photocrosslinking is used to crosslink the composition. The composition may further include a second crosslinkable molecule or polymer. The second crosslinkable molecule or polymer should have at least two crosslinkable groups capable of forming crosslinks with the crosslinkable moieties of the modified polysaccharide.

Proteins, oligonucleotides or pharmaceutical agents may be incorporated into the crosslinked composition. In some cases, the protein, oligonucleotide or pharmaceutical agent are incorporated by soaking the crosslinked compositions in a solution containing the protein, oligonucleotide or pharmaceutical agent. In other cases, the protein, oligonucleotide or pharmaceutical agent may be present in a solution containing uncrosslinked modified polysaccharide, with or without a second crosslinkable molecule. The composition is then crosslinked, for example, by photocrosslinking, to form a crosslinked composition including the protein, oligonucleotide or pharmaceutical agent.

In exemplary embodiments, the modified polysaccharide is a modified dextran molecule, and the second crosslinkable molecule is based on poly(ethylene glycol), for example poly(ethylene glycol) diacrylate (PEGDA).

The preparation of dextran-based hydrogels is illustrated using Dex-AI/PEGDA hydrogels, as shown below in FIG. 1. The objective of this step was to prepare the dextran-based hydrogels through the photocrosslinking of dextran-based precursors and PEGDA, using a long-wave (365 nm) UV lamp. A synthetic polymer precursor was introduced to have both synthetic and natural polymers occur in a single resulting hydrogel, thus obtaining tunable properties. Among synthetic polymer precursors, PEG has been extensively employed for many biomedical applications, due to its unique amphiphilic, biocompatible, but nonbiodegradable properties. Though PEG is not biodegradable, it can be readily excreted from the body via kidney and liver, thereby making it more suitable for biomedical applications. In addition, PEG has been employed to improve biocompatibility Zhang et al., *Biomaterials,* 2002, vol. 23, p. 2641-2648), to increase bioactivity (Muslim et al., *Carbohydr. Polym.,* 2001, vol. 46. p. 323-330), and to reduce immunogenicity (Hu et al., *Int. J. Biochem. Cell. Biol.,* 2002, vol. 34, p. 396-402).

Including a synthetic polymer, such as poly(ethylene glycol) in the crosslinked composition provides the capability to tune the properties of the resulting hydrogel. Tunable properties include mechanical properties, such as the swelling and modulus of the hydrogel. Other properties influenced by the type of synthetic polymer include crosslinking density and the release profile of any incorporated protein, oligonucleotide or pharmaceutical agent.

Properties of the crosslinked composition may be varied by varying the components of the composition, using a different modified polysaccharide, or changing the degree of substitution of one or more substituents on the modified polysaccharide. Other properties may be adjusted by varying the size of the polysaccharide, or the size of the second crosslinkable compound or polymer.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Terms listed in single tense also include multiple unless the context indicates otherwise.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

Methods for preparing, characterizing and using the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

EXAMPLES

Materials

Dextran (Dex, MW 70,000), allyl isocyanate (AI) and chloroacetic acid (AC) were purchased from Sigma Chemical Company (St. Louis, Mo.). Dextran was dried in a vacuum oven for 24 hours at 50° C. before use. Dimethyl sulfoxide (DMSO), Dibutyltin dilaurate (DBTDL), 2-bromoethylamine hydrobromide (BEAHB), triethylamine, maleic anhydride (AM), acryloyl chloride, PEG (MW 4,000), and other chemicals were purchased from Aldrich Chemical Company (Milwaukee, Wis.), and dried in a vacuum oven for 24 hours at room temperature before use. 2-Hydroxy-1-[4-(hydroxyethoxy)phenyl]-2-methyl-1-propanone was obtained from Ciba Specialty Chemicals Corporation (Tarrytown, N.Y.). Bovine serum albumin (BSA; MW 69,000) was purchased from Sigma Chemical Company. Cyclohexane was purchased from Fischer Scientific (Fairlawn, N.J.).

Statistics

All measurements of hydrogel properties—including swelling, degradation, biocompatibility, and release—were performed on duplicate samples with duplicate readings for each data point. Mechanical tests were performed on triplicate samples with triplicate readings for each data point. Bonferroni post tests and parametric two-way ANOVA tests were performed where appropriate (GraphPad Prism 4.02, GraphPad Software, San Diego, Calif.). Significance levels were determined using post tests between Dex-AI and each of its modifications, and were set at: *$p<0.05$, $p<0.01$, and *$p<0.001$. All graphical data is reported.

Example 1

Synthesis of Dextran Macromers

The synthesis of dextran macromers involved two steps, as shown in Scheme 1, for exemplary modified polysaccharide. Additional modified polysaccharides can be prepared in a similar manner.

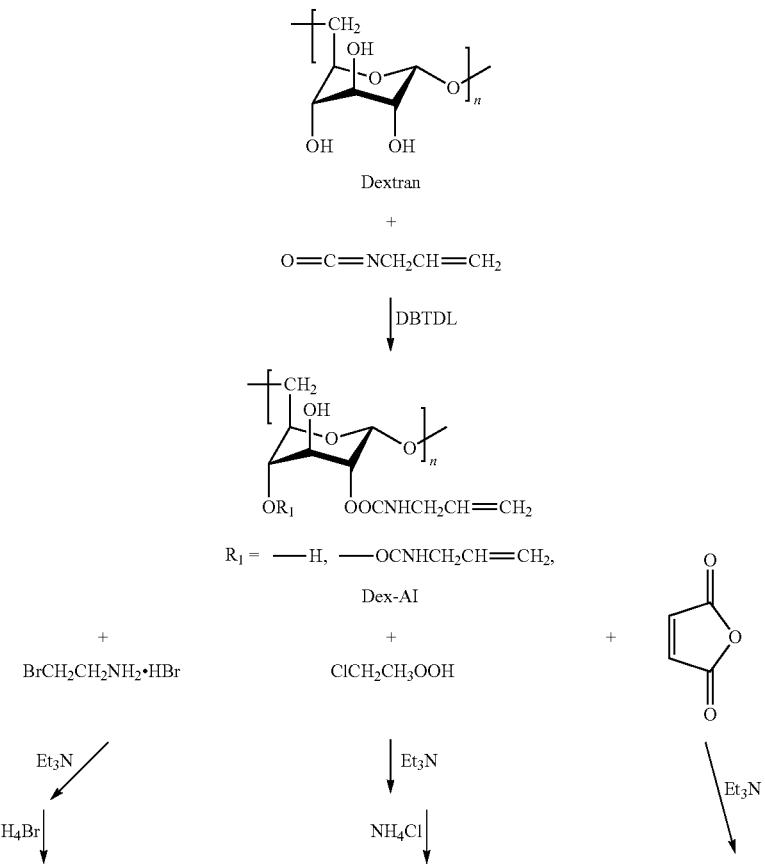

-continued

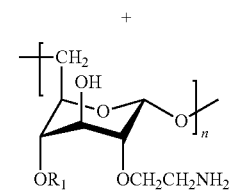

R₁ = —H, —CH₂CH₂NH₂
—OCNHCH₂CH=CH₂

Dex-AE

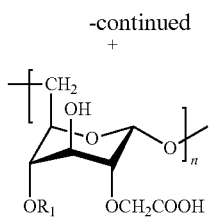

R₁ = —H, —CH2COOH
—OCNHCH₂CH=CH₂

Dex-AC

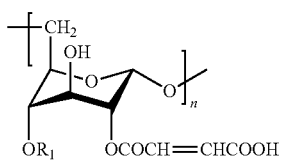

R₁ = —H, —COCH=CHCOOH
—OCNHCH₂CH=CH₂

Dex-AM

The first step was the incorporation of AI into dextran (to form Dex-AI), followed by further coupling of Dex-AI with BEAHB (to form Dex-AE), AC (to form Dex-AC), and AM (to form Dex-AM). Dex-AI was synthesized and characterized according to published methods (Zhang et al., "Synthesis and characterization of Biodegradable Hydrophobic-Hydrophilic Hydrogel Networks with a Controlled Swelling Property," *J. Polym. Sci. Polym. Chem.*, 2000, vol. 38, pp. 2392-2404). Briefly, AI was grafted onto dextran in the presence of DBTDL catalyst. Predried dextran (e.g., 3 g) was first dissolved in anhydrous DMSO under dry nitrogen gas. DBTDL catalyst (1.01 mL) was then injected into the solution, and AI (1.64 mL) was added dropwise to the above solution. The reaction was carried out for five hours at 30° C. The resulting polymer was precipitated in cold excess isopropanol. The product was further purified by dissolution and precipitation in DMSO and isopropanol, respectively. This resulting Dex-AI was then dialysized (molecular weight cut off [MWCO]: 1000 Da) against distilled water for three days, lyophilized for an additional three days, and stored at 4° C. in the dark for further use.

Three different molecules were introduced into Dex-AI. In the preparation of Dex-AE, Dex-AC and Dex-AM, Dex-AI reacted with BEAHB, AC, and AM, respectively. For example, Dex-AC was synthesized in the presence of triethylamine. Predried Dex-AI (3.0 g) was dissolved in anhydrous DMSO under a nitrogen atmosphere. Triethylamine (2.6 ml) was then injected into the above solution. Meanwhile, AC (1.8 g) was dissolved in anhydrous DMSO and then added dropwise to the above solution. This reaction solution was stirred for five hours at 30° C. The resulting Dex-AC polymer was obtained by precipitating into cold isopropyl alcohol. The product was further purified at least three times by dissolution and precipitation with DMSO and cold isopropyl alcohol, respectively. The resulting Dex-AC was dialysized (MWCO: 1000 Da) against distilled water for three days and lyophilized for an additional three days. Dex-AE and Dex-AM were prepared similarly. Dex-AE was also prepared by Sun et al. (*Carbohyd. Polym.* 2006, vol. 65, pp. 273-287).

Chemical Characterization

Figure 11A:
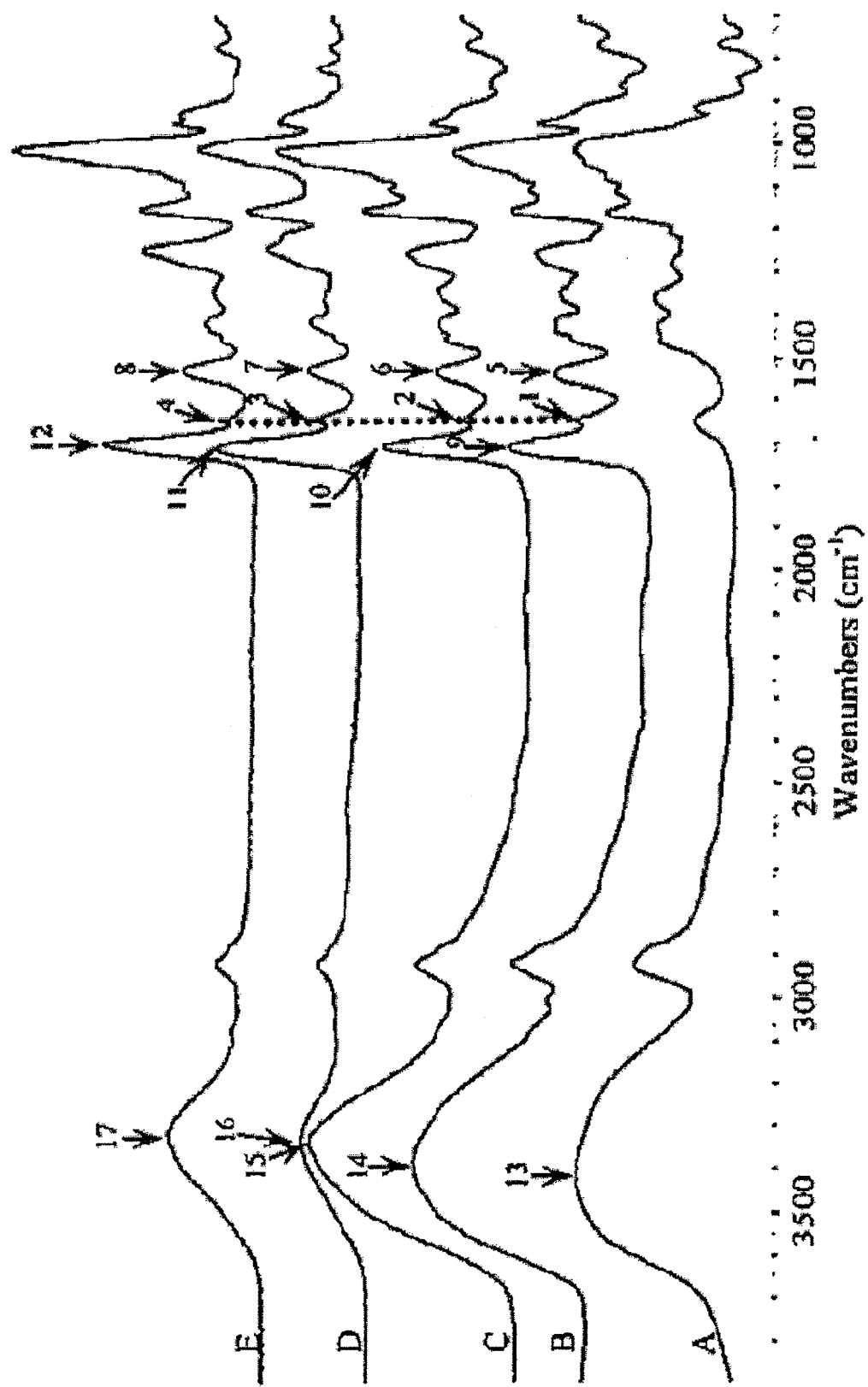
FIG. 11A shows the FTIR spectra with the following peak assignments: 1, 2, 3, & 4: ~1645 $cm^{-1}$; 5: ~1538 $cm^{-1}$; 6: ~1532 $cm^{-1}$; 7: ~1527 $cm^{-1}$; 8: ~1528 $cm^{-1}$; 9: ~1708 $cm^{-1}$; 10: ~1706 $cm^{-1}$; 11: ~1709 $cm^{-1}$; 12: ~1700 $cm^{-1}$; 13: ~3420 $cm^{-1}$; 14: ~3386 $cm^{-1}$; 15: ~3343 $cm^{-1}$; 16: ~3335 $cm^{-1}$; 17: ~3319 $cm^{-1}$.

Dextran, Dex-AI, Dex-AE, Dex-AM and Dex-AC were all characterized for their chemical structure by FTIR and $^1$H NMR (FIG. 11). For FTIR characterization, all samples were dried in a vacuum oven for at least 24 hours, and the collection was run on a Nicolet Magna 560 FTIR (Nicolet, Madison, Wis.) with a MIRacle ATR accessory (Pike, Madison, Wis.). For $^1$H NMR analysis, samples were dissolved in deuterated DMSO (DMSO-d6) at a concentration of 25 percent (w/v) and their spectra were recorded on a Varian INOVA 400 MHz spectrometer (Palo Alto, Calif.). The DMSO peak at 2.50 ppm was used as the reference line.

Results

Figure 11B:
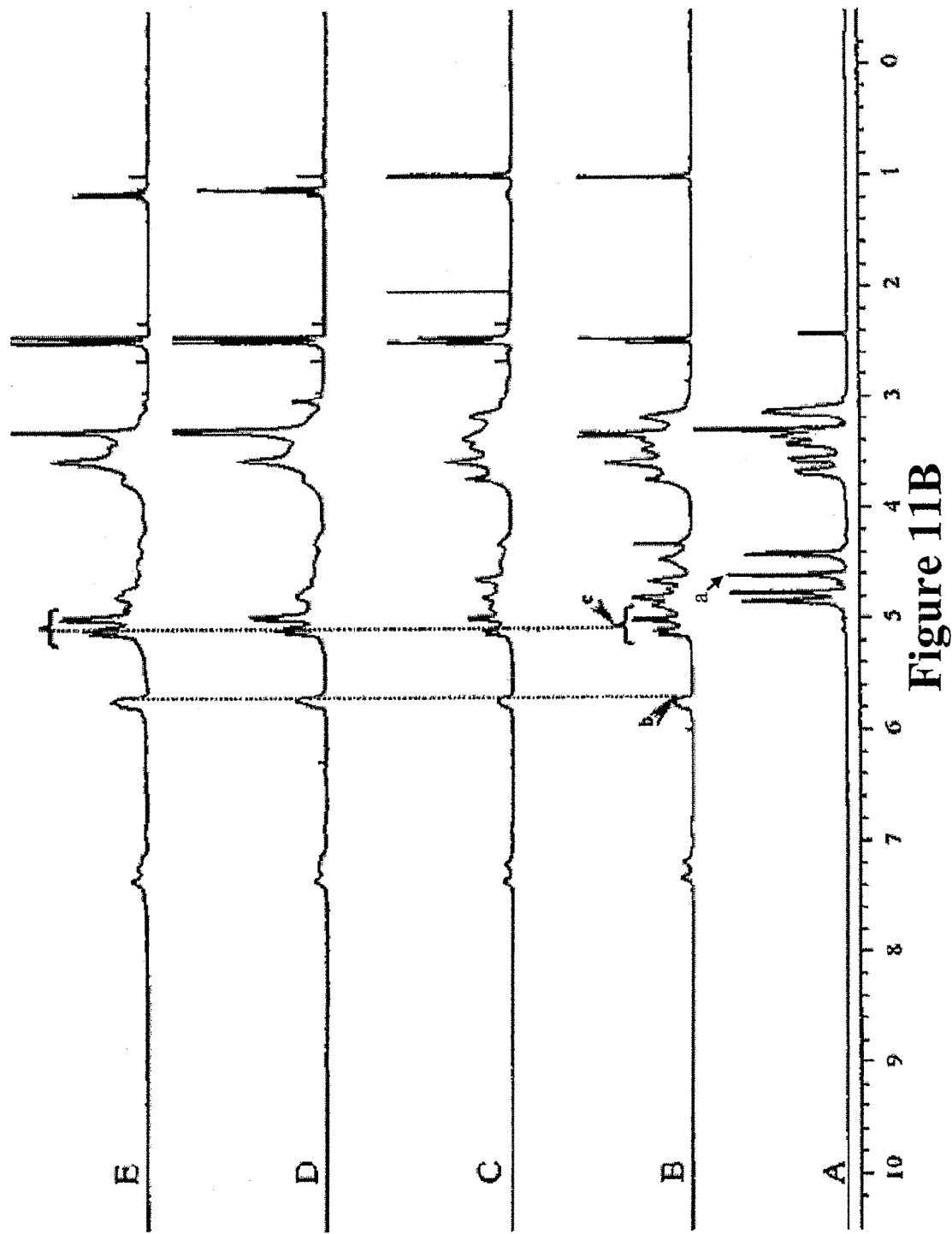
FIG. 11B shows the $^1$H-NMR spectra with the following chemical shifts: a: 4.68 ppm; b: 5.76 ppm; c: 4.99-5.15 ppm.

Different functional groups were introduce by reaction dextran (70 KDa) with a compound having crosslinkable moieties, for example AI, AC, AM, and BEAHB (to form the AE functional group), in two basic steps: the incorporation of AI, followed by the incorporation of amine (Dex-AE) or carboxylic acid (Dex-AC and Dex-AM) moieties. Scheme 1 summarizes this synthesis strategy. Dextran was reacted with AI (Dex-AI) in the presence of dibutyltin dilaurate (DBTDL) catalyst. Unreacted hydroxyl groups in the Dex-AI allowed the reaction with 2-bromoethylamine hydrobromide (BEAHB), chloroacetic acid (AC), and maleic anhydride (AM) to form Dex-AE, Dex-AC and Dex-AM, respectively. The Fourier transform infrared (FTIR) spectra of dextran were compared with Dex-AI, Dex-AE, Dex-AM and Dex-AC (FIG. 11A) and revealed the typical double-bond absorption bands at 1645 cm$^{-1}$. This confirmed that the C=C double bonds were successfully incorporated into the dextran. The peaks at 1708 cm$^{-1}$ and 1538 cm$^{-1}$, the characteristic amide I and amide II peaks of urethane groups of Dex-AI, shift in the spectra of Dex-AE, Dex-AM and Dex-AC when these three molecules are incorporated. The peak at 3420 cm$^{-1}$ is attributed the OH group of dextran, but it shifted to 3386 cm$^{-1}$ when AI was introduced. This peak also shifted as the other molecules were introduced. FIG. 11B shows the $^1$H Nuclear magnetic resonance ($^1$H NMR) spectra of the different macromers. The characteristic resonance peak at 4.68 ppm was the anomeric proton, which had no reactivity and did not change during any macromer reactions, while the other three adjacent peaks, from 4.49 to 4.91 ppm, were assigned to the three hydroxyl protons of dextran repeat units, and these peaks changed with each further modification. The vinyl end group peaks of all dextran derivatives appeared at 5.76 ppm and from 4.99 to 5.15 ppm. Both FTIR and NMR confirmed the chemical modification of the designed dextran macromers.

Example 2

Synthesis of Poly(Ethylene Glycol) Diacrylate (PEGDA)

PEGDA was synthesized as previously described (Sun et al., *Carbohyd. Polym.* 2006, vol. 65, pp. 273-287). Briefly, predried PEG (8.0 g) was dissolved in anhydrous benzene under a nitrogen atmosphere at 40° C. and then cooled down to room temperature. Triethylamine (1.19 mL) and acryloyl chloride (0.81 mL) were subsequently added. The reaction mixture was stirred for two hours at room temperature and then increased to 80° C. The resulting polymer was precipitated in hexane. It was further purified three times by dissolution and precipitation with benzene and hexane, respectively. The PEGDA was then dialysized (MWCO: 1000 Da) against distilled water for three days and then lyophilized for three days.

Example 3

Dex/PEGDA Hydrogel Preparation

To explore the effect of different derivatives on hydrogel properties, three different ratios of Dex/PEGDA: low (20/80), medium (40/60), and high (60/40) were examined. The preparation is illustrated using Dex-AI/PEGDA in FIG. 1A. The different modified dextran macromers and PEGDA were dissolved at different ratios (as described above) in phosphate buffered saline (PBS) containing 0.5 percent (w/w) 2-methyl-1-[4-(hydroxyethoxy)phenyl]-2-methyl-1-propanone (Irgacure 2959, I2959, Ciba). The mixture was pipetted into a sterile mold (50 μL volume per well, to obtain discs measuring 4 mm in diameter×2 mm thick), and photopolymerized (approximately 10 mW/cm$^2$ of UV light for ten minutes; BlakRay). The resulting hydrogels were washed in distilled water for 24 hours to remove unreacted precursors before further characterization. Compared to previous method (Sun et al., *Carbohydrate Polymers*, 2006; vol. 65, no. 3, pp. 273-287), which takes 16-20 hours to form complete gels, this improved method is more suitable for tissue engineering applications (Ferreira et al., *Biomaterials*, 2007, vol. 28, no. 17, pp. 2706-2717; Gerecht et al., *Proc Natl Acad Sci USA*, 2007, vol. 104, no. 27, pp. 11298-11303).

FIG. 1B shows the conversion (wt %) of each type of synthesized hydrogels which decreased with the increase in dextran-derivatives in the hydrogel feed ratios. For example, the conversion of Dex-AI/PEGDA decreased from 93.52% to 82.21% when Dex-AI increased from 20% to 60%. This conversion reduction could be attributed to lower reactivity of the double bonds (C=C) in dextran derivatives than those in PEGDA (Sun et al., *Carbohydrate Polymers*, 2006; vol. 65, no. 3, pp. 273-287; Guo et al., K, *Journal of Polymer Science Part A-Polymer Chemistry*, 2005, vol. 43, no. 17, pp. 3932-3944, and thus the increase in dextran derivative led to a decreased conversion. The conversions of Dex-AE/PEGDA hydrogels show similar results to previous published results (Sun et al., *Carbohydrate Polymers*, 2006; vol. 65, no. 3, pp. 273-287), but their conversions are lower than the other three hydrogels at the same ratios. Interestingly, the further addition of double bonds into Dex-AI, i.e., Dex-AM, does not increase the conversion. The increased of degree of substitution of double bonds does not affect the gel structure significantly, but only changes the gelation rate (Sun et al., *Journal of Biomaterials Science-Polymer Edition*, 2009, vol. 20, no. 14, pp. 2003-2022). In this case, the addition of double bond by incorporating maleic anhydride does not increase the conversion either. As all hydrogels are prepared in the same size of molds, the lower conversion at higher feed ratio will give rise to a lose network structure.

Example 4

Swelling Study of Dex/PEGDA Hydrogels

The swelling ratio of dextran-based hydrogels was gravimetrically determined. Predried hydrogel specimens were immersed in distilled water at room temperature. The swollen hydrogels were removed from water at predetermined intervals and weighed after wiping off excess water from the surface with a wet filter paper. The swelling ratio was then calculated according to the following formula:

$$\text{Swelling ratio} = ((W_{s,t} - W_d)/W_d) \times 100\% \qquad (1)$$

where $W_d$ is the weight of dry hydrogels, and $W_{s,t}$ is the weight of swollen hydrogels at time t. The hydrogels were assumed to reach a state of swelling equilibrium when there was no difference in swelling ratio between two adjacent intervals.

The swelling of all hydrogels reached equilibrium at around ten hours, while significant differences in swelling volumes were observed as dextran content increased (FIG. 2A(i-iii)). Maximum swelling volume increased with increasing dextran content (FIG. 2A(iv)). Two-way ANOVA analysis revealed that swelling progress over time depended significantly on dextran backbone modification as dextran content increased in Dex-AI/PEGDA, Dex-AM/PEGDA and Dex-AC/PEGDA hydrogels (p<0.001).

Example 5

Enzymatic Biodegradation of Dex/PEGDA Hydrogels

Hydrogel samples (n=2) were prepared as described above, weighed, and incubated in PBS buffer (pH=7.4) with two dextranase concentrations (0.5 unit/ml and 5.0 unit/ml) at 37° C. for 24 hours. Hydrogel samples were removed from the solutions, washed with distilled water, and lyophilized in a FreeZone freeze dryer (2.5 L; Labconco, Kansas City, Mo.) at −48° C. for three days and weighed. The extent of biodegradation was estimated from the weight loss of the polymer based on the following equation:

$$W_1 = ((W_o - W_d)/W_o) \times 100\% \qquad (2)$$

where $W_o$ is the original weight of the hydrogel samples, and $W_d$ is the weight of dry hydrogel samples after being degraded for 24 hours.

Enzymatic study revealed that all hydrogel materials were degradable at faster rates as dextran content increased (FIG. 2B). Small or nonsignificant differences were observed in degradation rates of different dextran modifications at the same Dex/PEGDA ratio. Two-way ANOVA analysis revealed that hydrogel degradation rates were independent of chemical modification (p>0.05).

Example 6

Mechanical Study of Dex/PEGDA Hydrogels

The mechanical properties of the hydrogel samples (n=3) were determined using a Q800 Dynamic Mechanical Analyzer (TA Instruments, New Castle, Del.) in unconfined submersion compression mode. Briefly, the diameter of each swollen hydrogel disk was determined using a digital caliper, and the sample was immersed in a PBS bath between unconfined parallel compression platens. Hydrogel samples were compressed at a rate of 10 percent of thickness/min until failure or until they reached 60 percent of their initial thickness. The modulus was then calculated as the ratio of the stress-strain curve at low strain (<25 percent strain), i.e., the linear portion of the curve.

Figure 3A:
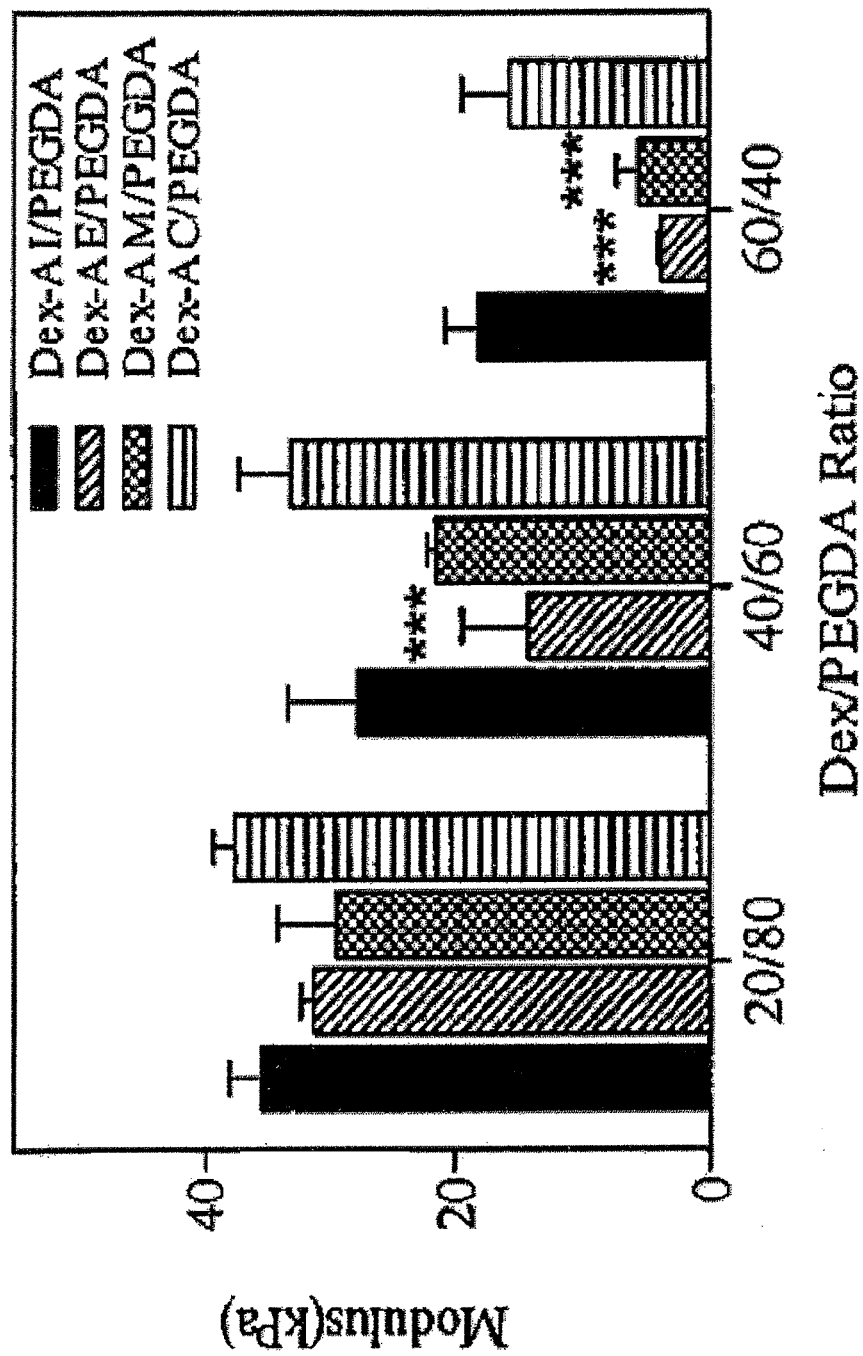
FIG. 3A is a graph of compression modulus of dextran hydrogels at three different Dex/PEGDA ratios, demonstrating decrease in modulus with increase in dextran content.

The modulus of the Dex/PEGDA hydrogels decreased with an increase in the Dex/PEGDA ratios (FIG. 3A). Hydrogels at 20/80 Dex/PEGDA ratios were found to have a higher modulus. However, when the dextran macromer in the hydrogel component increased to 60 percent, a dramatic drop in the modulus of Dex-AE/PEGDA and Dex-AM/PEGDA was observed. For example, increasing Dex-AI content in the hydrogel from 20 to 40 percent and then to 60 percent resulted in modulus reduction of 23.6 percent and 48.3 percent, respectively, while modulus reductions of 54.1 percent and 87.7 percent were observed with increased Dex-AE content in the hydrogels.

Example 7

Determination of Crosslinking Density

The crosslinking density of the swollen hydrogels was evaluated using established methods (Guo et al., *Biomaterials* 2007, vol. 28, pp. 3284-3294; Peppas et al., *J. Biomed. Mater. Res.*, 1985, vol. 19, pp. 397-411). The average molecular weight between crosslinks ($\overline{M_c}$) can be calculated from the following equation:

$$\overline{M_c} = \frac{3\rho_p RT}{E}(v_{2,s})^{1/3} \quad (3)$$

where $\rho_p$ is the density of polymers, R is the gas constant, T is the absolute temperature, $v_{2,s}$ is the polymer volume fraction at swollen state, and E is the elastic modulus. The crosslinking density ($\rho_\chi$) is defined as:

$$\rho_\chi = \frac{\rho_p}{\overline{M_c}} \quad (4)$$

From (3) and (4), the crosslinking density was calculated from the following equation:

$$\rho_\chi = \frac{E}{3RT}(v_{2,s})^{-1/3} \quad (5)$$

The polymer volume fraction ($v_{2,s}$) was calculated as previously reported (Guo et al., *Biomaterials* 2007, vol. 28, pp. 3284-3294; Peppas et al., *J. Biomed. Mater. Res.*, 1985, vol. 19, pp. 397-411):

$$v_{2,s} = \frac{W_{a,d} - W_{c,d}}{W_{a,s} - W_{c,s}} \quad (6)$$

where $W_{a,d}$ and $W_{c,d}$ are the dried hydrogel weight in air and cyclohexane, respectively, while $W_{a,s}$ and $W_{c,s}$ are the hydrogel weight in air and cyclohexane after having swollen in water, respectively. Then, the crosslinking density can be calculated from the following equation:

$$\rho_\chi = \frac{E}{3RT} \times \left(\frac{W_{a,d} - W_{c,d}}{W_{a,s} - W_{c,s}}\right)^{1/3} \quad (7)$$

Utilizing modulus and swelling data, the crosslinking density of the Dex/PEGDA hydrogels was calculated as previously demonstrated (N. A. Peppas and H. J. Moynihan, 1985; K. Guo and C. C. Chu, 2007). We found that network structure density decreased with the increase of dextran content. Furthermore, at the 60/40 Dex/PEGDA ratio, Dex-AI/PEGDA and Dex-AC/PEGDA were shown to have network structures that were significantly denser than Dex-AE/PEGDA and Dex-AM/PEGDA (FIG. 3B).

Example 8

Biocompatibility of Dex/PEGDA Hydrogels

In vitro: Cell proliferation was detected either by daily cell count or by using the XTT kit (Sigma), according to the manufacturer's instructions and as previously demonstrated (Gerecht et al., *Proc. Natl. Acad. Sci. USA*, 2007, vol. 104, pp. 11298-11303; Gerecht et al., *Biomaterials*, 2007, vol. 28, pp. 4826-4835). Briefly, endothelial cells (EC) (C166 line) from American Type Culture Collection (ATCC) were cultured in the presence of macromer solution (10 µl/ml culture medium) and counted daily or incubated for four hours in medium containing 20 percent (v/v) {2,3-bis(2-methoxy-4-nitro-5-sulfophenyl)-5-[(phenylamino)carbonyl]-2H-tetrazolium hydroxide} (XTT) solution. For analysis, 150 µl of the medium was removed, placed it in a 96-well plate, and read it in a microplate reader at 450 nm.

Figure 4A:
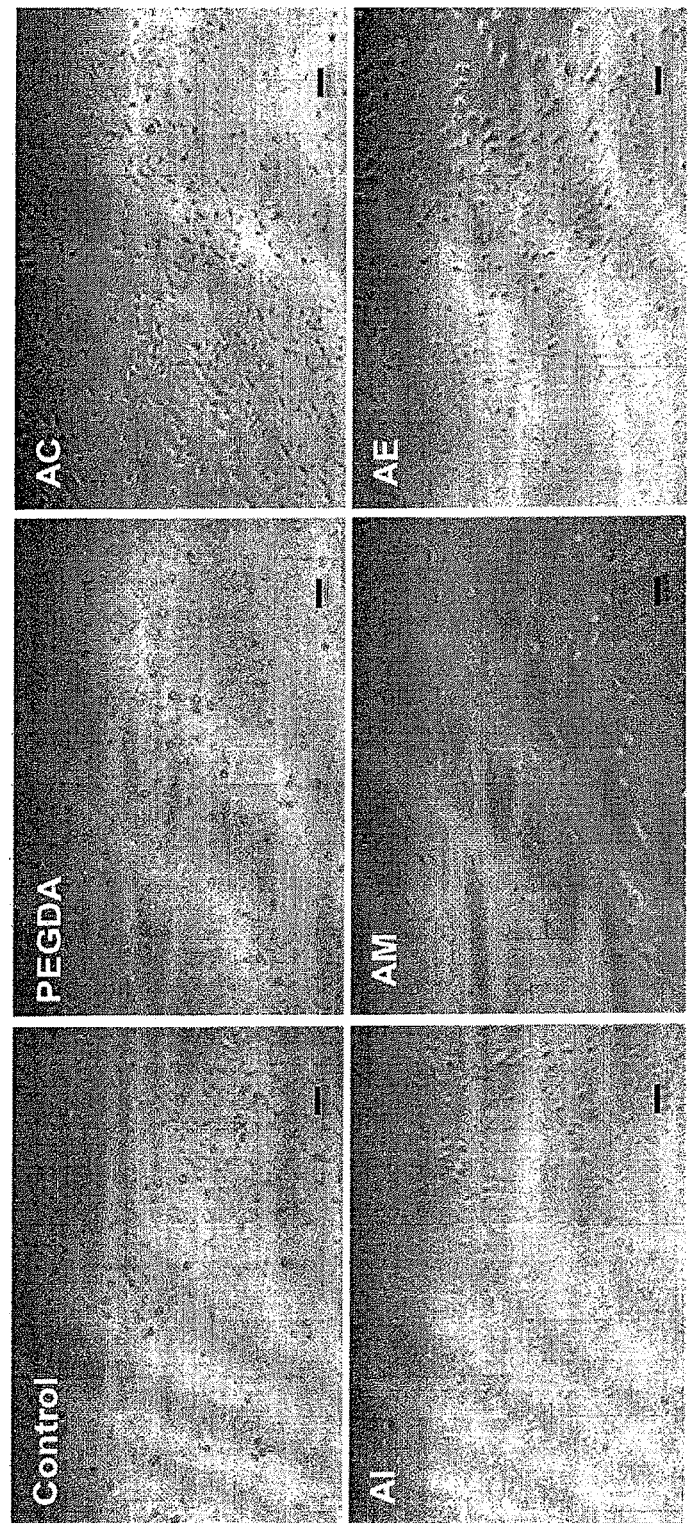
FIG. 4A illustrates in vitro toxicity of Dex/PEGDA monomers on ECs with light microscopy images of ECs grown in Petri dish in the absence (control) or presence of 10 µl/ml of PEGDA (control) or different Dex/PEGDA (60/40) prepolymers. Adhesion and spreading of ECs were observed under all conditions, with lower cell numbers in cultures containing Dex-AM/PEGDA.
Figure 4B:
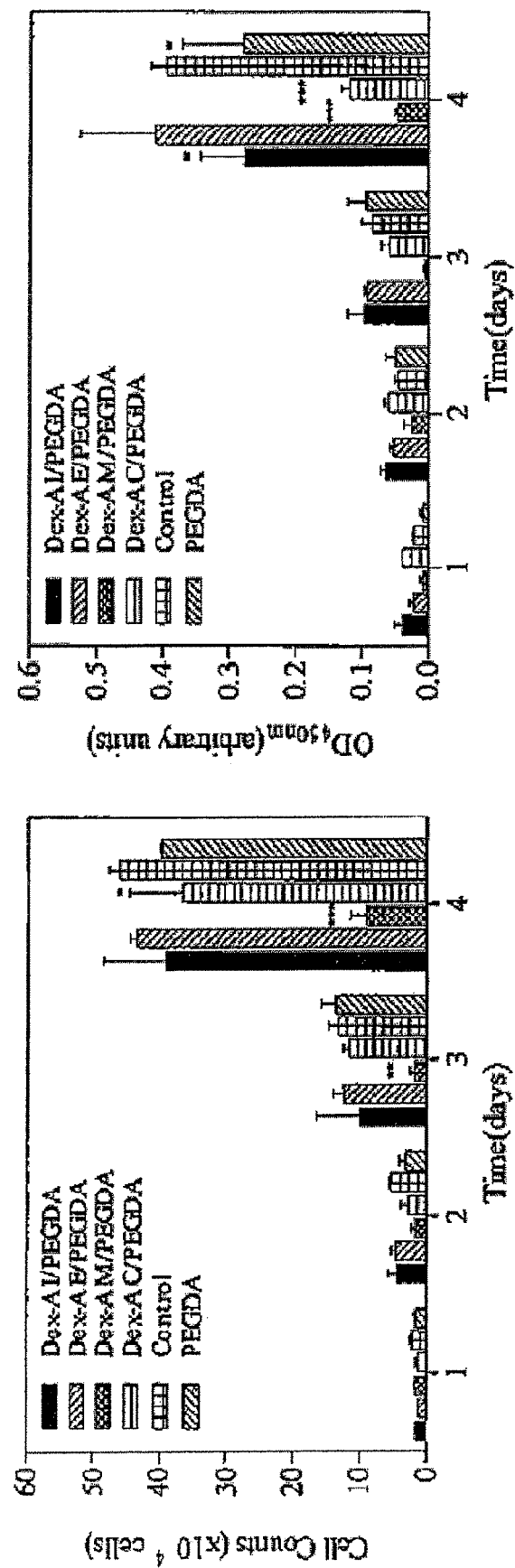
FIG. 4B illustrates in vitro toxicity of Dex/PEGDA monomers on ECs with cell proliferation graphs quantified by cell count (left) and an XTT cell proliferation assay (right) showing significant reduction in cell activity in cultures supplemented with Dex-AM/PEGDA, as compared to cells grown in control conditions and with all other Dex-based hydrogels.

In vitro results: In order to explore the opportunities to use the newly developed dextran-based hydrogels in biomedical applications, it was important to assess any toxicity of the modified dextran macromer. As the precursor molecules cannot completely form hydrogels during photocrosslinking, some precursor residues remain within the gels. The unreacted macromers may be released during swelling. The toxicity that may result from the presence of free dextran macromer was investigated. Endothelial cell (EC) line C166 was subcultured and propagated in a Petri dish in growth medium containing macromer solution with the highest dextran content (i.e., a 60/40 Dex/PEGDA ratio). After 24 hours, ECs attached and spread under all conditions; however, a low number of ECs was observed in medium containing Dex-AM/PEGDA macromer (FIG. 4A). Comparison of the proliferation rates revealed toxic effects of Dex-AM/PEGDA macromer, while the rate of cell proliferation in medium containing Dex-AI/PEGDA, Dex-AE/PEGDA, and Dex-AC/PEGDA was indistinguishable from that in control mediums (FIG. 4B).

In vivo: Dex/PEGDA hydrogels were prepared in the shape of a disc (2 mm thick×4 mm diameter) under sterile conditions. Female Lewis rats (n=2) (Charles River Laboratories, Wilmington, Mass.) weighing 200 to 250 g were housed separately and had access to water and food ad libitum. Animals were cared for according to the approved protocols of the Committee on Animal Care of the Johns Hopkins University, in conformity with the NIH guidelines for the care and use of laboratory animals (NIH publication #85-23, revised 1985). The animals were anaesthetized using continuous 2 percent isoflurane/$O_2$ inhalation. Two sample implantations per time point were performed. Three small midline incisions on the dorsum of the rat were made, and the implants were introduced in lateral subcutaneous pockets created by blunt dissection. All animals remained in good general health throughout the study, as assessed by their weight gain. At each predetermined time point (1 and 3 weeks), rats were sacrificed, and the implanted scaffolds were removed en bloc with the surrounding tissue (approximately 10×10 mm). The samples were fixed and processed for histology as described below.

Dex/PEGDA hydrogel explants were fixed with Accustain (Sigma-Aldrich, St. Louis, Mo.) for 24 hours, dehydrated in graded ethanol (70 to 100 percent), embedded in paraffin, serially sectioned using a microtome (4 μm), and stained with hematoxylin and eosin (H&E).

Figure 4C:
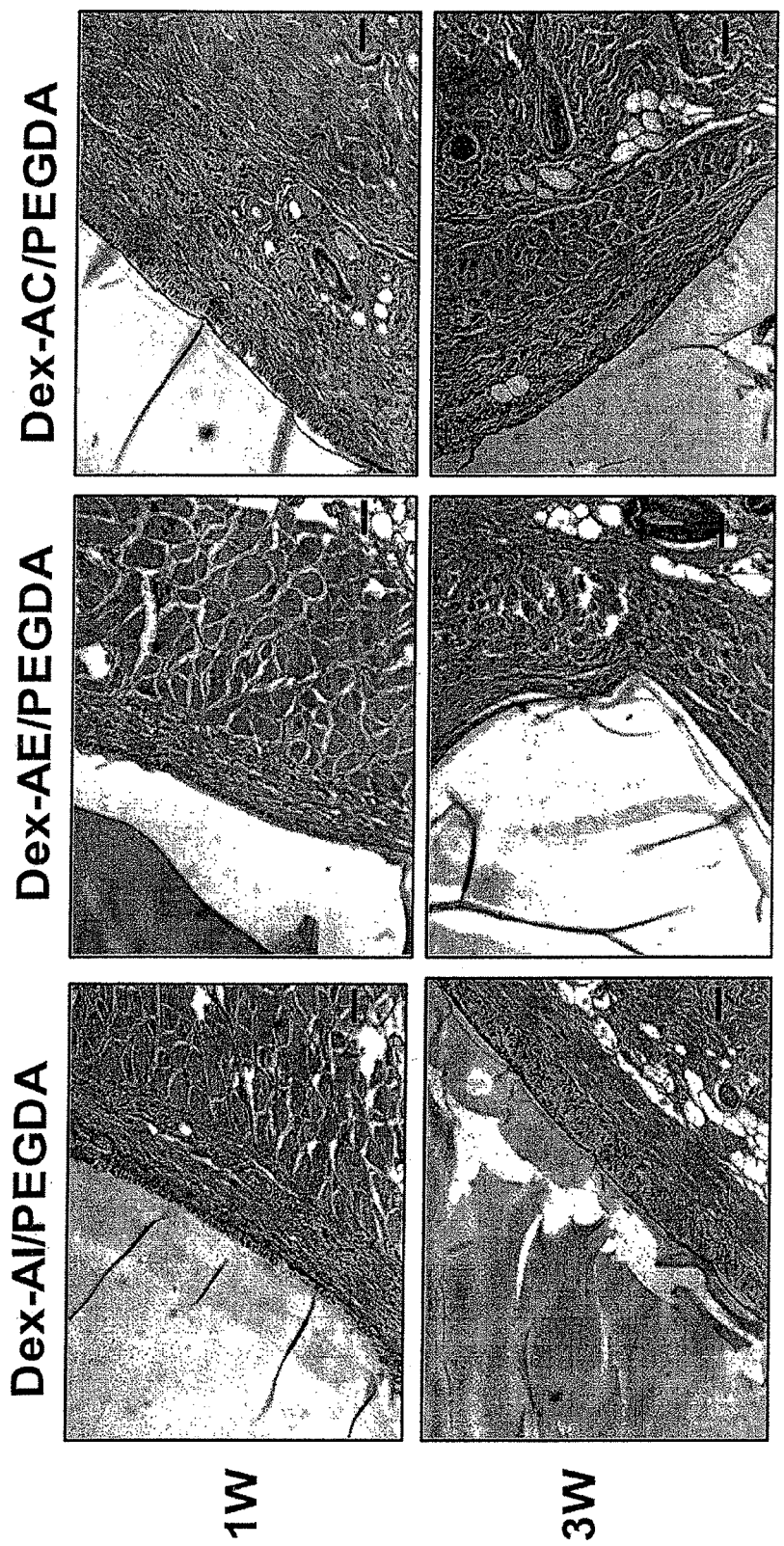
FIG. 4C illustrates in vivo biocompatibility of DEX/PEGDA hydrogels with images showing how subcutaneous transplantation of Dex-AI/PEGDA, Dex-AE/PEGDA, and Dex-AC/PEGDA (40/60 ratio) elicited immune response after 1 to 3 weeks (1 W, 3 W) as demonstrated by H&E staining of histologic sectioning.

In vivo results: To investigate the biocompatibility of our newly developed Dex/PEGDA hydrogels, we prepared Dex-AI/PEGDA, Dex-AE/PEGDA, and Dex-AC/PEGDA hydrogels (Dex-AM/PEGDA hydrogels were excluded due to their high toxicity in vitro), and implanted them subcutaneously in rats for up to three weeks. As some of the Dex/PEGDA hydrogels at high dextran content levels (i.e., at the 60/40 ratio) are very soft (as indicated by the modulus results shown above), experiments used the medium Dex/PEGDA ratio (i.e., 40/60) at which hydrogels are manageable for transplantation purposes. In all three hydrogels we observed a foreign body reaction with a dense macrophage layer, and several multinucleated giant cells adjacent to the hydrogels followed immediately by a loose collagen-mediated granulation layer (FIG. 4C). All three hydrogels showed decreasing granulation layer thickness after three weeks (FIG. 4C) indicating that these hydrogels have no adverse effect on local tissue in the wound healing process. However, an enlarged inflammatory response was observed one week after implantation of the Dex-AC/PEGDA hydrogels and, to a lesser extent in the Dex-AI/PEGDA and Dex-AE/PEGDA hydrogels, as determined by a greater number of macrophages present in the layer (FIG. 4D(i-iii)). The elevated inflammatory response in the Dex-AC/PEGDA hydrogels observed at week one was not observed at the three-week time point (FIG. 4D(iv)). A large number of dilated blood vessels presented in the granulation layer were observed indicating an active healing response in all hydrogels (FIG. 4E). Overall, the foreign body reaction for all Dex/PEGDA hydrogels over a three-week period, is similar to that previously reported for biocompatible materials (Wang et al., *Nat. Biotech.*, 2002, vol. 20, no. 6, pp. 602-606; Wang et al., *J. Biomed Mater Res A*, 2003, vol. 66A, no. 1, pp. 192-197).

Overall, the active zone showed a decreasing inflammatory response for all Dex/PEGDA hydrogels over a three-week period, similar to that previously reported for biocompatible materials (Wang et al., *Nat. Biotechnol.*, 2002, vol. 20, pp. 602-606; Wang et al., *Biomed. Mater. Res. A,* 2003, vol. 66, 192-197). The inflammatory response of Dex-AI- and Dex-AE-based hydrogels at all time points was similar to that previously reported for PLGA and PGS (Wang et al., *Nat. Biotechnol.*, 2002, vol. 20, pp. 602-606; Wang et al., *Biomed. Mater. Res. A,* 2003, vol. 66, 192-197), which are known to be highly biocompatible.

Example 9

VEGF$_{165}$ Release Studies

Hydrogel samples were prepared as described above in example 3, except that 165 amino acid form of vascular endothelial growth factor (VEGF$_{165}$) (Pierce Biotechnology, Rockford, Ill.) was mixed with macromer (1 μg/100 μL) in the mold prior to photopolymerization, resulting in a final VEGF concentration of 20 ng per 1 mg of dry gel. The solution was then UV irradiated for ten minutes to allow the gel to form. The gels were carefully removed from the mold, immersed in 2.0 ml of PBS, and incubated at 37° C. At predetermined intervals, 400 μl of the PBS solution was collected and 400 μl of blank PBS solution was added back into the immersion medium to maintain the total solution volume at 2.0 ml. The samples were stored at −80° C. before ELISA (Pierce Biotechnology) analysis was conducted according to the manufacturer's instructions. Briefly, VEGF$_{165}$ in the ELISA kit standards and samples was captured on the anti-human VEGF$_{165}$ antibody-coated microplate. After removing unbound proteins, biotinylated antibody reagent was added to bind to the secondary site on VEGF$_{165}$. Then, to produce a colorimetric signal, streptavidin-horseradish peroxidase was added to bind to TMB. Standards were prepared according to the manufacturer's instructions. Plate washing was performed three times between each step to remove any excess reagents. The colorimetric signal was detected using a UV microplate spectrophotometer (SpectraMax Plus, Molecular Devices, Sunnycale, Calif.) at absorbance wavelengths of 450 nm and 550 nm. The standard curve was interpolated to determine the amount of VEGF$_{165}$ at each predetermined time point. Results are presented in terms of cumulative release as a function of time:

$$\text{Cumulative Release } (\%) = \left(\sum_{t=0}^{t=t} M_t / M_\infty\right) \times 100 \qquad (8)$$

where $$\sum_{t=0}^{t=t} M_t$$

is the cumulative amount of released VEGF from the hydrogel at time t, and M$_\infty$ is the initial amount of loaded VEGF in the hydrogel.

Results

Figure 5A:
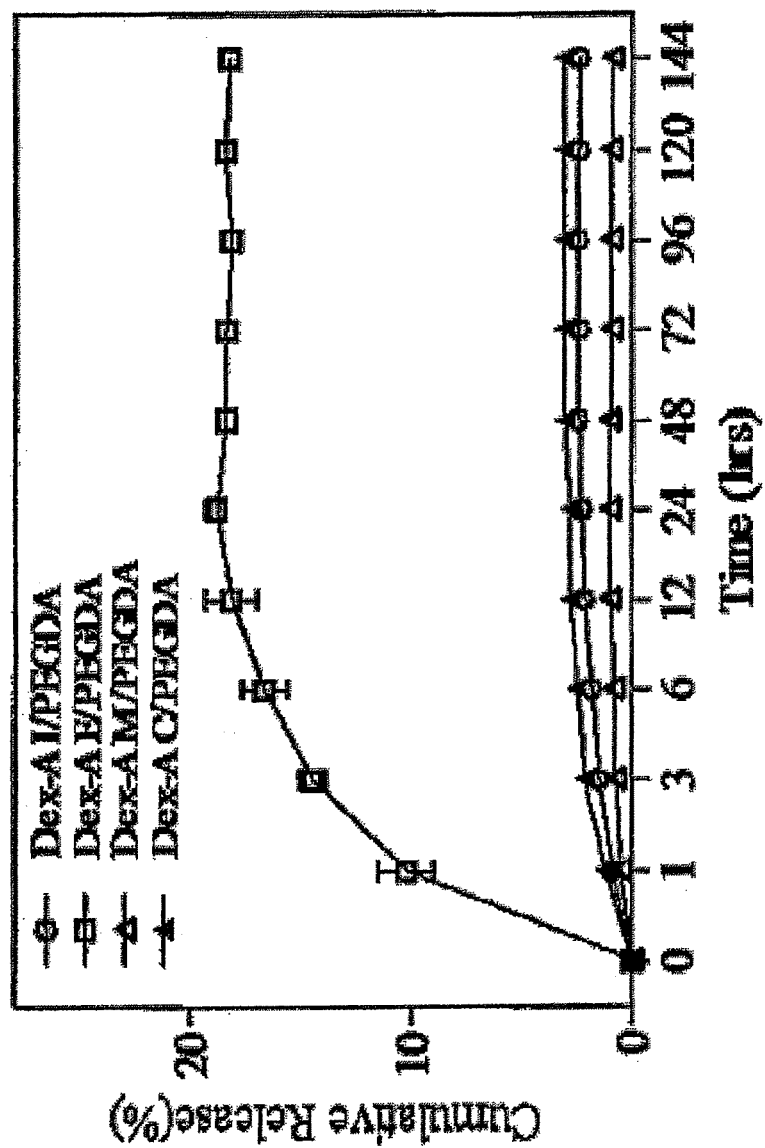
FIG. 5A shows cumulative release of $VEGF_{165}$ from Dex/PEGDA hydrogel (40/60 ratio) showed approximately 20% release from Dex-AE/PEGDA hydrogel, and only up to about 3% release from other hydrogels. Values are plotted as the cumulative percent release measured using quantitative analyses. Values shown are means±SD.

In these studies, VEGF showed two distinct release patterns (FIG. 5A). Dex-AE/PEGDA showed an obvious fast release, in which about 20 percent of the VEGF was released during the first 24 hours, followed by a continuous release of smaller amounts. However, we found that the VEGF release profiles of the Dex-AI/PEGDA, Dex-AC/PEGDA, and Dex-AM/PEGDA hydrogels were similar, with no evidence of burst release; in these hydrogels, only about 3 percent of the VEGF was released within the first 24 hours. This result was unexpected based on previous results with Dex-AE/PEGDA hydrogels. The structural properties of Dex-AE/PEGDA, which has the highest swelling rate, the lowest modulus, and the lowest crosslinking density, provide a possible explanation for this effect.

Swelling/diffusion and degradation are the major drug release mechanisms for biodegradable hydrogels. The biodegradation-based release mechanism would be more important because swelling/diffusion alone could not completely release large molecule drugs from hydrogels. To assess whether VEGF release from Dex-AE has potential for future biomedical application, we tested Dex-AE/PEGDA and VEGF-releasing-Dex-AE/PEGDA using subcutaneous transplantation as described above.

Figure 5B:
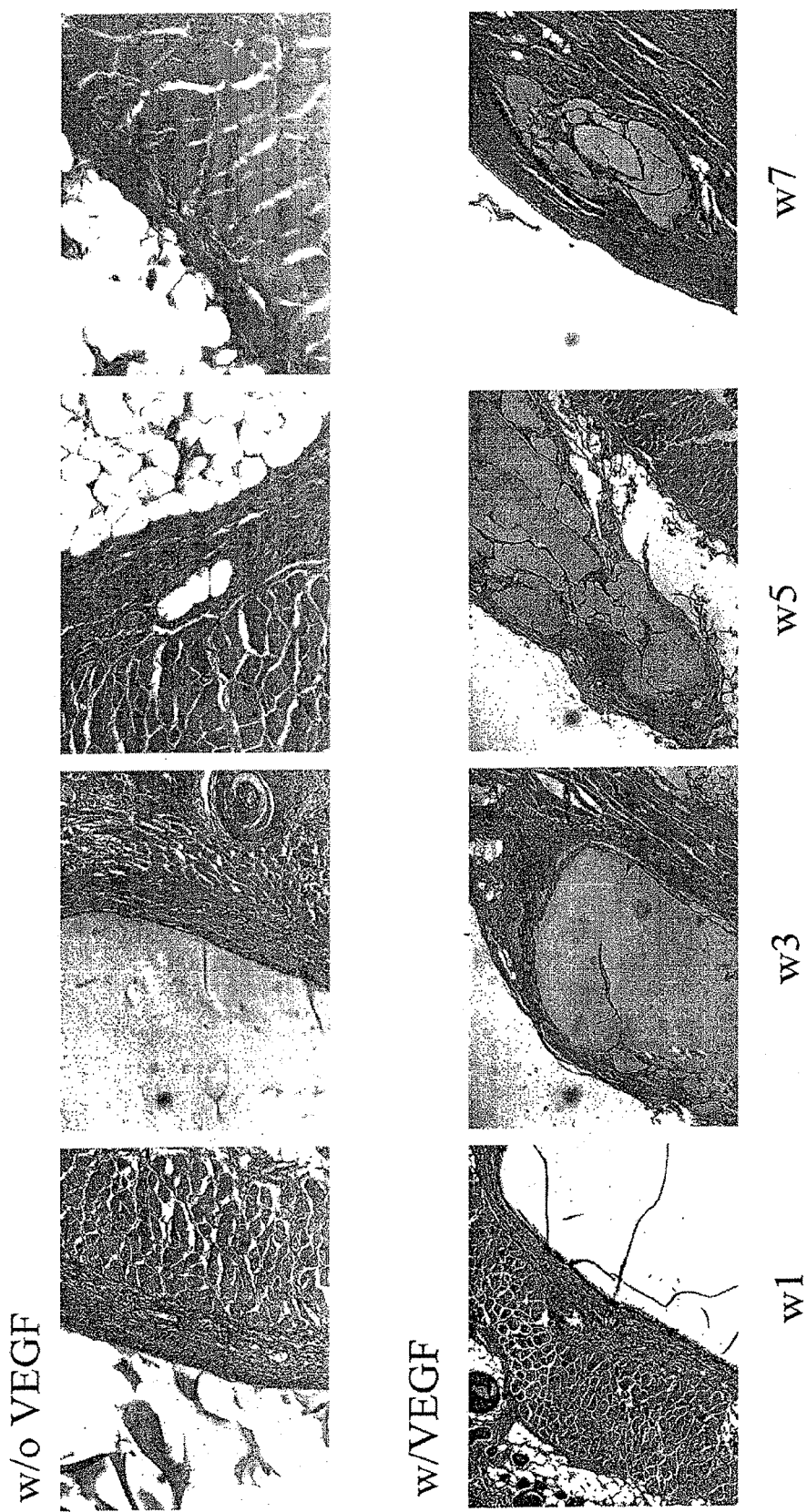
FIG. 5B shows low magnification images of H&E staining for the in vivo subcutaneous study showing Dex-AE/PEGDA hydrogels with VEGF (w/VEGF) and without VEGF (w/o VEGF) at week 1 (w1), week 3 (w3), week 5 (w5), and week 7 (w7).

FIG. 5B shows the subcutaneous study up to 7 weeks at low magnification. The hydrogel-loaded with VEGF showed distinct tissue ingrowth in 5 weeks, while the hydrogel alone did not show such tissue ingrowth. This indicates VEGF can promote tissue ingrowth, and tissue ingrowth will further facilitate the hydrogel degradation.

After one week of implantation, invasion of macrophages to the VEGF-releasing-Dex-AE/PEGDA hydrogel was observed at high magnification (FIG. 5C) After seven weeks of implantation, there was little to no granulation tissue evident in both Dex-AE/PEGDA and VEGF-releasing-Dex-AE/PEGDA; both displayed a very thin layer of macrophages immediately surrounding the gel suggesting the healing process of the surrounding tissue is complete (FIG. 5D). Fragmented hydrogel engulfed with macrophages and blood vessels were observed after seven weeks of implantation of the VEGF-releasing Dex-AE/PEGDA hydrogels, indicating tissue ingrowth and hydrogel degradation (FIG. 5E).

Example 10

One major issue of other dextran hydrogels are slow degradation and less tissue ingrowth. The discovery that hydrogels having too much crosslinking density retard the degradation and tissue penetration, may explain this problem. A second problem is the limit on the amount of dextran that can be used to form a stable hydrogel, limiting the degradation rate and extent. Previously, stable hydrogels were formed only at Dextran/PEGDA ratios between 70/30 and 0/100 (Sun et al., *Carbohydrate Polymers*, 2006; vol. 65). In this study, newly prepared hydrogels were examined having Dex-AE and PEGDA at three different ratios of Dex-AE/PEGDA: low (40/60), medium (60/40), and high (80/20). The new Dex-AE have much lower degree of substitution of allyl isocyanate groups, which incorporate double bonds and provide the crosslinking sites. Differences in physical and biological properties of the hydrogels are found, including swelling, mechanics, vascular endothelial growth factor release, and in vivo vascular formation.

Synthesis of Dextran Macromers Having Low Degree of Substitution

Dry dextran (e.g., 3.0 g) was dissolved in anhydrous DMSO (30 ml) under dry nitrogen gas. DBTDL catalyst (0.1 ml) was injected into the solution dropwise, and AI (0.16 ml) was then added dropwise. The reaction mixture was stirred at 30° C. for 6 hours. The resulting polymer was precipitated in cold excess isopropanol. The product was further purified by dissolution and precipitation in DMSO and isopropanol, respectively. The degree of substitution (DS, the number of substitution groups per anhydroglucose unit) of AI obtained under this condition is 0.09, as determined by NMR.

To synthesize Dex-AE, Dex-AI prepared above was further reacted with 2-bromoethylamine hydrobromide (BEAHB) in the presence of triethylamine. Dry Dex-AI (2.0 g) was dissolved in anhydrous DMSO (24 ml) under dry nitrogen gas. Triethylamine (11.2 ml) was injected into the above solution. BEAHB (3.75 g) was dissolved in DMSO (10 ml) and then added to the above solution dropwise. This reaction solution was stirred at 50° C. for 6 hours. The reaction mixture was then filtered to remove precipitated $Et_3NH_4Br$. The resulting Dex-AE polymer was obtained by precipitating the filtered solution into excess cold isopropyl alcohol. The product was further purified at least 3 times by dissolution and precipitation in DMSO and cold isopropyl alcohol, respectively. The final product was dried at room temperature under vacuum overnight before further use. The resulting Dex-AE was dialysized (MWCO: 1000 Da) against distilled water for seven days and lyophilized for an additional three days.

Example 11

Dex/PEGDA Hydrogel Preparation

The different modified dextran macromers and PEGDA were dissolved at different ratios (as described above) in phosphate buffered saline (PBS) containing 0.1% (w/w) 2-methyl-1-[4-(hydroxyethoxy)phenyl]-2-methyl-1-propanone (Irgacure 2959, I2959, Ciba). The mixture was pipetted into a sterile mold (80 μL, volume per well, to obtain discs measuring 4 mm in diameter×2 mm thick), and photopolymerized (approximately 10 mW/cm² of UV light for ten minutes; BlakRay). The resulting hydrogels were washed in distilled water for 24 hours to remove unreacted precursors before further characterization.

Hydrogels Having 80% Dextran

As discussed previously, hydrogels having high amounts of polysaccharide (i.e. greater than 80%) are advantageous. Previously, though, solid hydrogels formed only at Dextran/PEGDA ratios between 70/30 and 0/100 (Sun et al., *Carbohydrate Polymers*, 2006; vol. 65). In this study, newly prepared hydrogels were examined having Dex-AE and PEGDA at three different ratios of Dex-AE/PEGDA: low (40/60), medium (60/40), and high (80/20). The low degree of substitution allows preparation of hydrogels having 80% or more dextran, as summarized in Table 1 below. For hydrogels noted 1× in the table below, Dex-AI was prepared from a weight ratio of unmodified dextran and allyl isocyanate of about 2:1 at different temperatures, resulting in different degrees of substitution. As a reference, Dex-AI with a degree of substitution of 0.35 in the table below refers to the material prepared in EXAMPLE 1. The Dex-AI was further modified with BEAHB to prepare Dex-AE macromers. When photopolymerized with PEGDA (4000 MW) at a ratio of 80/20, no hydrogels were formed in any 1× samples. When Dex-AI having lower degree of substitution were used, hydrogels were formed. In the table below, 0.5× refers to the relative amount of allyl isocyanate use in the reaction Dex-AI reaction, corresponding to a weight ratio of unmodified dextran to allyl isocyanate of about 4:1 (2:0.5). Likewise, 0.25× refers to a weight ratio of dextran to allyl isocyanate of about 8:1 (2:0.25). 0.1× refers to a weight ratio of about 20:1 (2:0.1), which is the same Dex-AI described in Example 10, having a degree of substitution of 0.09. 0.05× refers to a weight ratio of about 40:1 (2:0.05).

|  | 0.05X | 0.1X | 0.25X | 0.5X | 1X | 1X | 1X |
|---|---|---|---|---|---|---|---|
| Reaction Temp.(° C.) | 30 | 30 | 30 | 30 | 30 | 25[a, b] | 45[b] |
| DS | <0.05 | 0.09 |  |  | 0.35 | 0.25 | 0.77 |
| 80/20 | −[1] | + | ± | ± | −[2] | −[3] | −[4] |
| 100/0 | − | ± | − | − | − | − | − |

Note:
The precursor concentration was 0.1 g/mL; + stands for gel can be formed within 10 min, − stands for gels cannot form, ± stands for gel can form, but are not as solid.
[1] at 80/20, the precursor did not form hydrogels within 10 minutes, but forms in 20-30 minutes.
[2,3,4] at 80/20, the precursor did not form hydrogels even at longer time.

Example 12

Swelling Study of Dex/PEGDA Hydrogels

Figure 6:
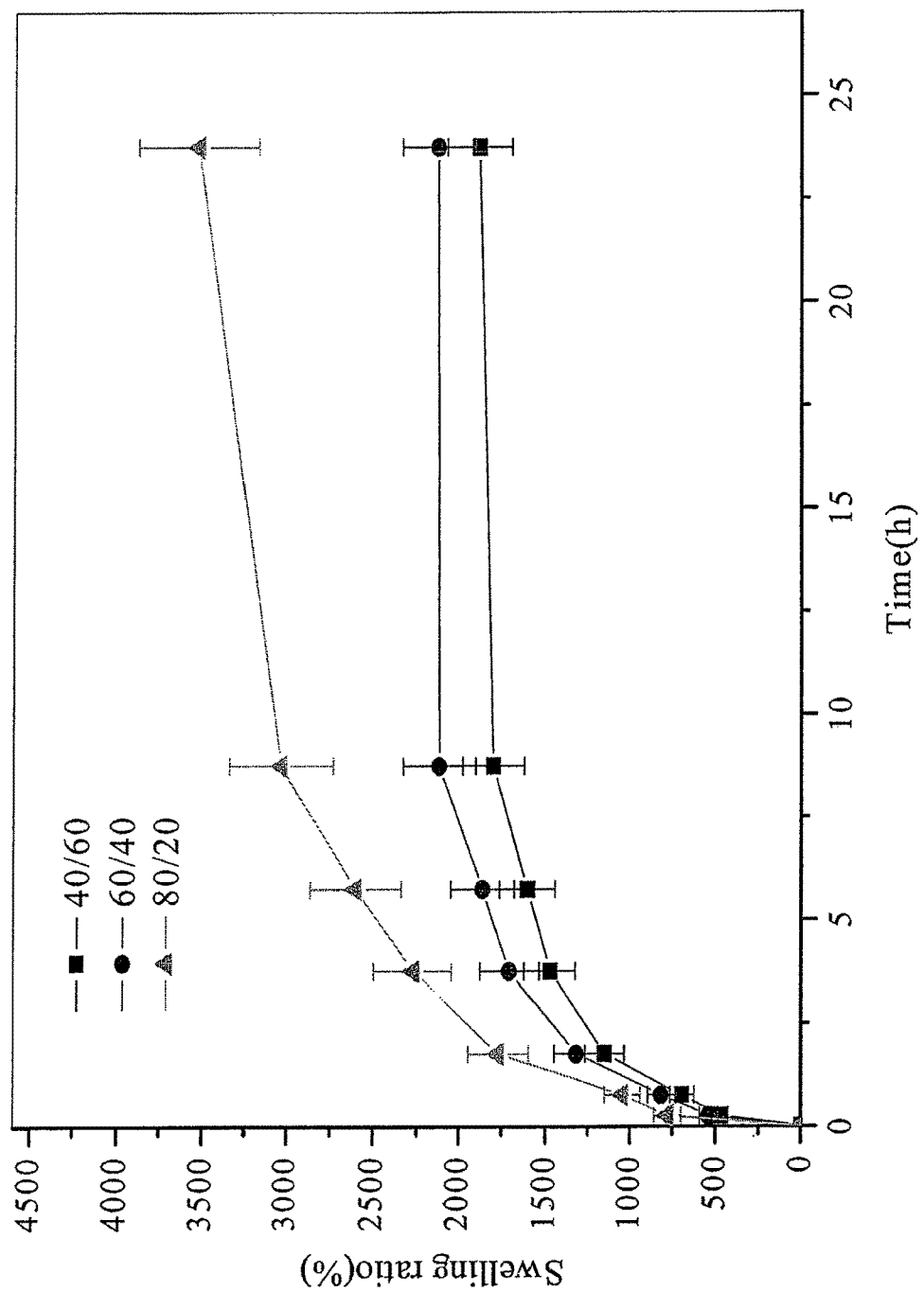
FIG. 6 shows the swelling property of low degree of substitution Dex-AE/PEGDA at different feed ratios.

Swelling study determines the water retention capability of hydrogels. The degree of substitution of double bonds is approximately 25% of Dex-AE prepared in EXAMPLE 3. To examine if such modification has any effect on the properties of newly formed hydrogels, the water retention capability was tested by studying swelling ratio of the different Dex-AE/PEGDA hydrogels. It was found that the hydrogels reached equilibrium swelling state within approximately 10 hours, except that the hydrogel at the feeding ratio of 80/20 showed slight increase in swelling ratio. The increase in Dex-AE component in the feeding ratio led to faster and higher swelling (FIG. 6). Compared to the material of EXAMPLE 3, these hydrogels show much higher swelling ratios. For example, for Dex-AE/PEGDA at the ratio of 60/40, the swelling is 2100% while the Dex-AE/PEGDA from EXAMPLE 3 has a swelling ratio of 1300%. This increase in swelling ratio is surprising in view of recent data showing that changes in the degree of substitution of allyl isocyanate are not expected to have a pronounced effect on the swelling of hydrogels (Sun et al., *Journal of Biomaterials Science—Polymer Edition*, 2009, vol. 20, no. 14, pp. 2003-2022).

Previous studies show that the swelling ratio of Dex-AE/PEGDA hydrogel is mostly dominated by their structures. This increased swelling ratio may be attributable to the relatively loose structure of the newly prepared hydrogels. The decrease in the amount of double bonds reduced the bonding sites, causing the lower crosslinking density.

Example 13

Mechanical Study of Dex/PEGDA Hydrogels

Figure 7:
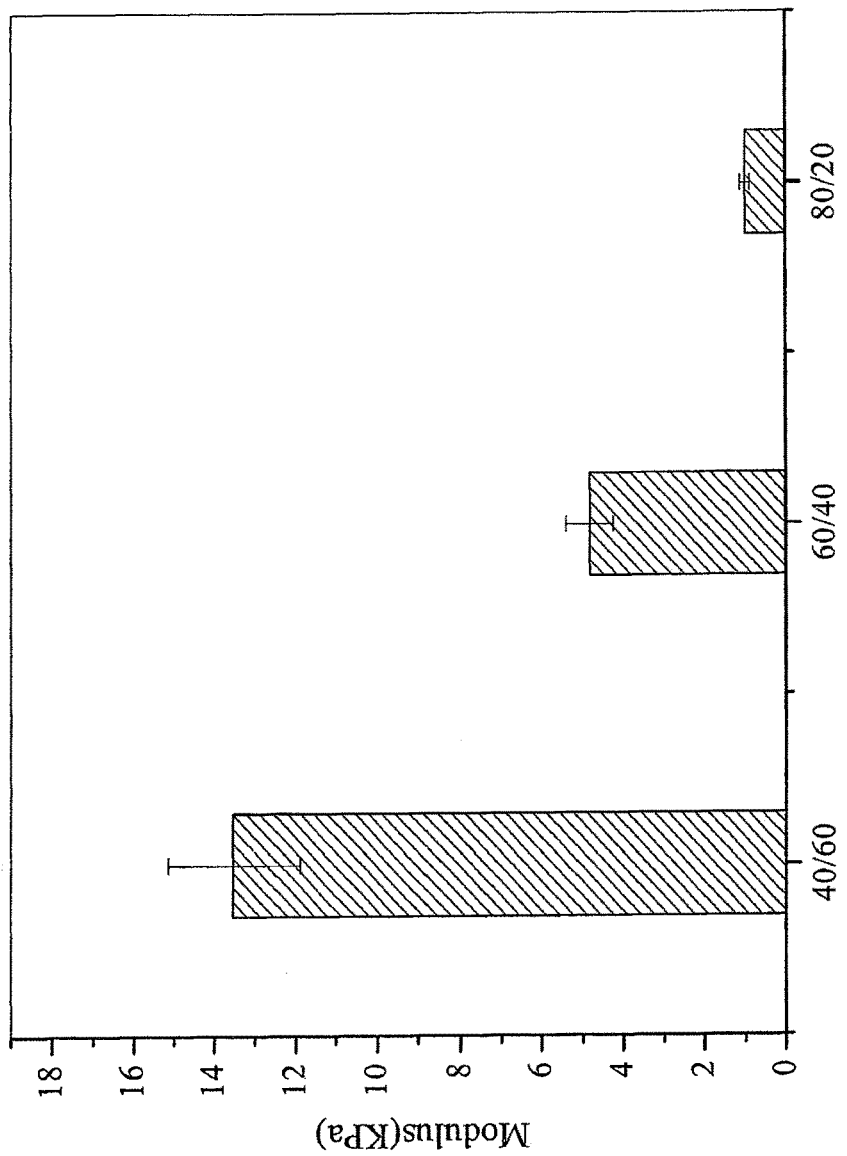
FIG. 7 shows the mechanical study of low degree of substitution Dex-AE/PEGDA hydrogels with different feeding ratios.

Appropriate mechanical strength is critical for 3D hydrogel scaffolds. It is important to make some scaffolds with a wide range of controllable strength. FIG. 7 shows that the increase in Dex-AE in the hydrogel feeding component caused the decrease in mechanical strength. Prior studies revealed that the increase in Dex-AE component leads to decreased crosslinking density, and we further confirmed this change with different of DS of double bonds. Compared with previous results, the mechanical stress at 40/60 and 60/40 is very close and they are around 13~15 MPa and 4~5 MPa, respectively. Obviously, the decrease in the amount of double bonds from Dex-AE did not affect the hydrogel structure significantly. This result may suggest that only a small amount of photocrosslinking is necessary to provide mechanical strength. Higher degrees of crosslinking usually gives rise to brittle structures, which can destroy the mechanical properties. As discussed previously, it is advantageous to reduce the UV exposure time of the hydrogel-forming compositions. With low degree of substitution Dex-AI, solid hydrogels having a ratio of 80/20 Dex-AE/PEGDA were formed in 10 minutes of photocrosslinking.

Example 14

Growth Factor Release

Hydrogel samples were prepared as described in EXAMPLE 10 above, except that $VEGF_{165}$ (Pierce Biotechnology, Rockford, Ill.) was mixed with macromer (1 μg/100 μL) in the mold prior to photopolymerization, resulting in a final VEGF concentration of 20 ng per 1 mg of dry gel. The solution was then UV irradiated for ten minutes to allow the gel to form. The gels were carefully removed from the mold, immersed in 2.0 ml of PBS, and incubated at 37° C. At the same time, equivalent amount of VEGF was incubated in a separated vial and their bioactivity was test at the same predetermined intervals as cumulative test. At predetermined intervals, we collected 400 μl of the PBS solution and added 400 μl of blank PBS solution back into the immersion medium to maintain the total solution volume at 2.0 ml. The samples were stored at −80° C. before we performed an ELISA (Pierce Biotechnology) analysis, which we did according to the manufacturer's instructions.

Figure 8:
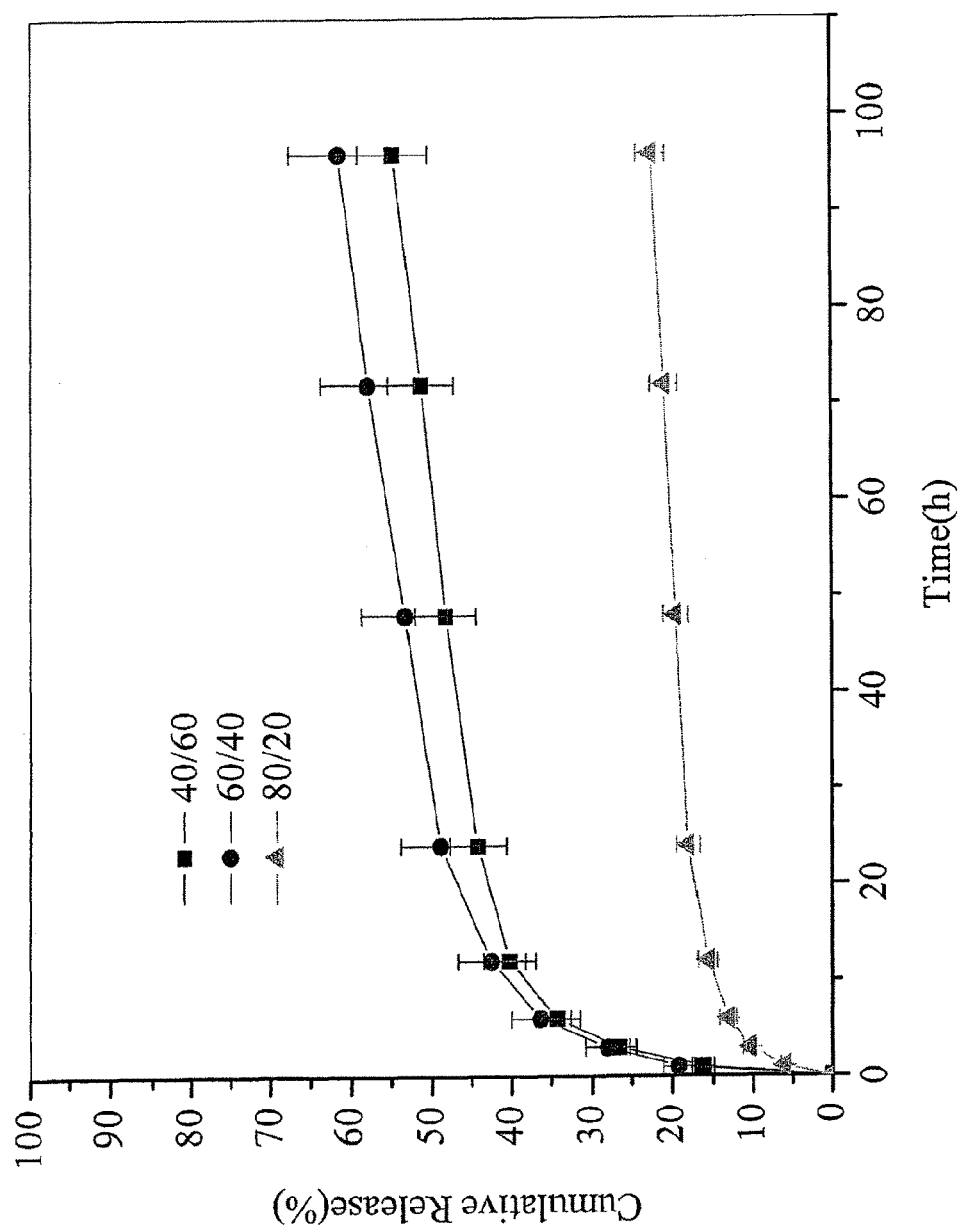
FIG. 8 shows the cumulative release of VEGF from low degree of substitution Dex-AE/PEGDA hydrogels.

Briefly, $VEGF_{165}$ in the ELISA kit standards and samples were captured on the anti-human $VEGF_{165}$ antibody-coated microplate. After removing unbound proteins, biotinylated antibody reagent was added to bind to the secondary site on $VEGF_{165}$. Then, to produce a colorimetric signal, streptavidin-horseradish peroxidase was added to bind to TMB. Standards were prepared according to the manufacturer's instructions. Plate washing was performed three times between each step to remove any excess reagents. The colorimetric signal was detected using a UV microplate spectrophotometer (SpectraMax Plus, Molecular Devices, Sunnycale, Calif.) at absorbance wavelengths of 450 nm and 550 nm. The standard curve was interpolated to determine the amount of $VEGF_{165}$ at each predetermined time point. Results are presented in terms of cumulative release as a function of time Growth factors are important regulators for vasculogenesis. However, most growth factors will lose their bioactivities, while ELISA only detects the biologically active VEGF. Thus, in this study, we use the bioactive VEGF as the actual reference at each time point. FIG. 8 shows that VEGF has a burst release from the hydrogel at the ratio of 40/60 and 60/40, about 35% of VEGF was release during the first 10 hours, while over 50% VEGF was release within 96 hours. However, 18% VEGF was released from the material of EXAMPLE 3. The hydrogel at 60/40 shows faster release than the one at the ratio of 40/60 during the rest of release test. However, the hydrogel at the ratio of 80/20 does not show any burst release, and the continuous release only reached about half of VEGF from the other two hydrogels.

Drug release process may be driven by diffusion and degradation or both. Before degradation takes place, diffusion is the release mechanism. During the early release stage, drug release is thus mostly dominated by the swelling. As discussed above, the swelling of the newly synthesized hydrogels is much higher than prior hydrogels, which is attributed to the higher release. In addition, the revised method is more accurate in determining the release. A previous study ignored the bioactivity issue of VEGF, and used original loading amount of VEGF, instead of actual bioactive VEGF. The present method is thus more representative of the actual release. Surprisingly, the VEGF release from 80/20 hydrogel show much less amount than from other two gels. One possible explanation might be attributed to the existence of amine groups. The increase in Dex-AE in the hydrogel feeding ratio increases the amount of amine groups, which may increase interactions with protein-based drugs, enhance the interaction between hydrogel and VEGF, and thus reduce the burst release and prolong the VEGF release period.

Example 15

In Vivo Vascularization of Dex-AE/PEGDA Hydrogels

Dex-AE/PEGDA hydrogels were prepared in the shape of a disc (2 mm thick×4 mm diameter) under sterile conditions. Female Lewis rats (n=2) (Charles River Laboratories, Wilmington, Mass.) weighing 200 to 250 g were housed separately and had access to water and food ad libitum. Animals were cared for according to the approved protocols of the Committee on Animal Care of the Johns Hopkins University, in conformity with the NIH guidelines for the care and use of laboratory animals (NIH publication #85-23, revised 1985). The animals were anaesthetized using continuous 2% isoflurane/$O_2$ inhalation. Two sample implantations per time point were performed. We made three small midline incisions on the dorsum of the rat, and the implants were introduced in lateral subcutaneous pockets created by blunt dissection. All animals remained in good general health throughout the study, as assessed by their weight gain. At each predetermined time point (1 and 3 weeks), rats were sacrificed, and the implanted scaffolds were removed in bloc with the surrounding tissue (approximately 10×10 mm). The samples were fixed and processed for histology as described below.

Histology

Dex-AE/PEGDA hydrogel explants were fixed with Accustain (Sigma-Aldrich, St. Louis, Mo.) for 24 hours, dehydrated in graded ethanol (70 to 100%), embedded in paraffin, serially sectioned using a microtome (4 µm), and stained with either hematoxylin and eosin (H&E) or immunohistochemistry for CD31 and ED1.

Results

Subcutaneous studies (EXAMPLE 9) showed that Dex-AE/PEGDA hydrogels release VEGF and can promote tissue ingrowth, and that tissue ingrowth will further facilitate the hydrogel degradation. However, as tissue engineering scaffolds, this time period is still too long for some in vivo applications. Modified Dex-AE with a lower degree of AI substitution was then utilized, to potentially increase hydrogel degradation and tissue ingrowth.

Figure 9:
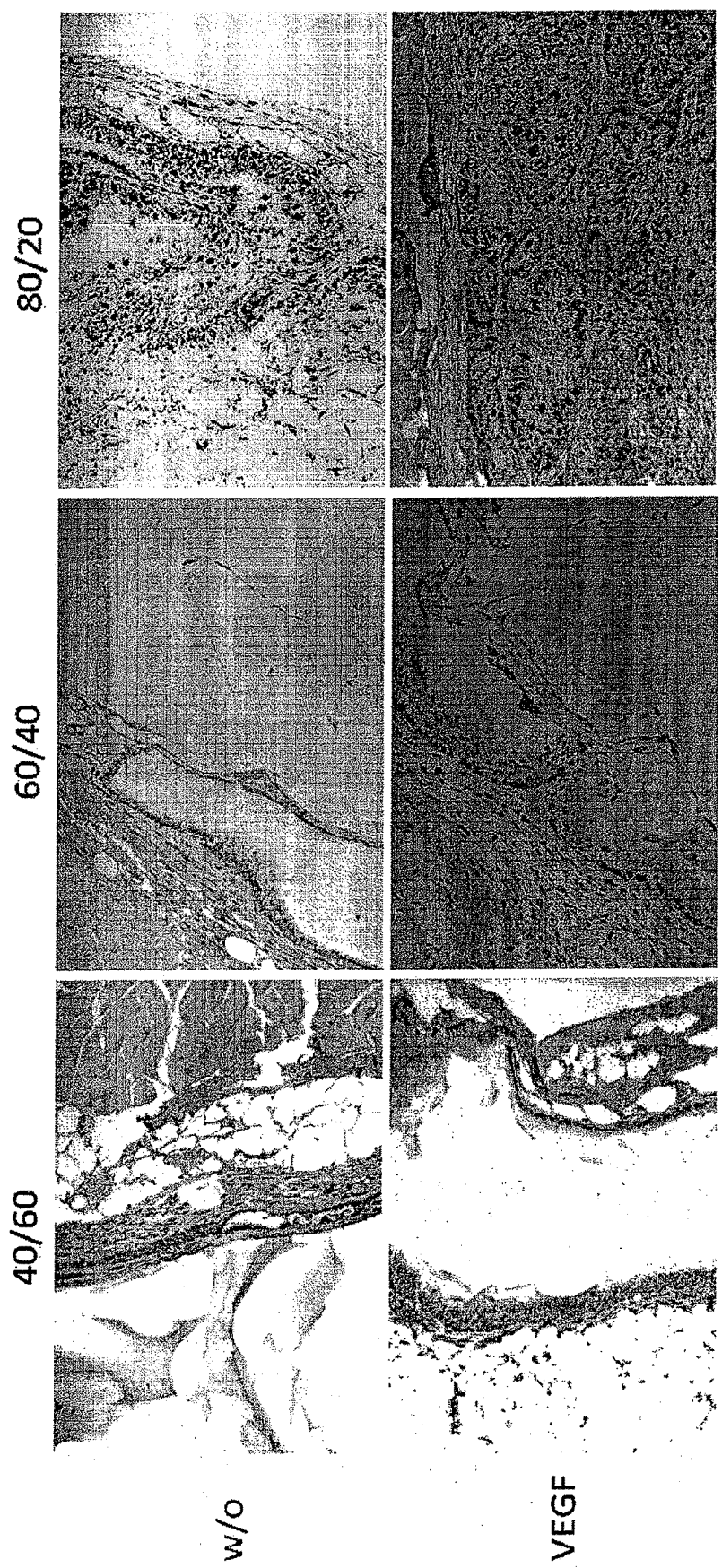
FIG. 9 shows different ratios of low degree of substitution Dex-AE/PEGDA hydrogels at week 5 stained with ED1, which shows the macrophage response to the implant. Result indicates rapid response along with greater tissue in-growth and gel fragmentation at feeding ratio of 80/20.

FIG. 9 illustrates results obtained from different ratios of low degree of substitution Dex-AE/PEGDA hydrogels at week 5 stained with ED1, showing the macrophage response to the implant. These result demonstrate rapid response along with greater tissue in-growth and gel fragmentation at feeding ratio of 80/20. Previous studies indicated that higher ratios of dextran lead to a loose structure. Among the three hydrogels in this study, 80/20 has the loosest structure, and may facilitate tissue ingrowth more than than others. Meanwhile, in this Dex-AE/PEGDA hydrogel system, PEGDA is not degradable, and dextranase only degraded dextran, an increase in dextran component thus led to a faster degradation. Therefore, a greater tissue ingrowth was observed within the 80/20 hydrogel in this study.

Figure 10:
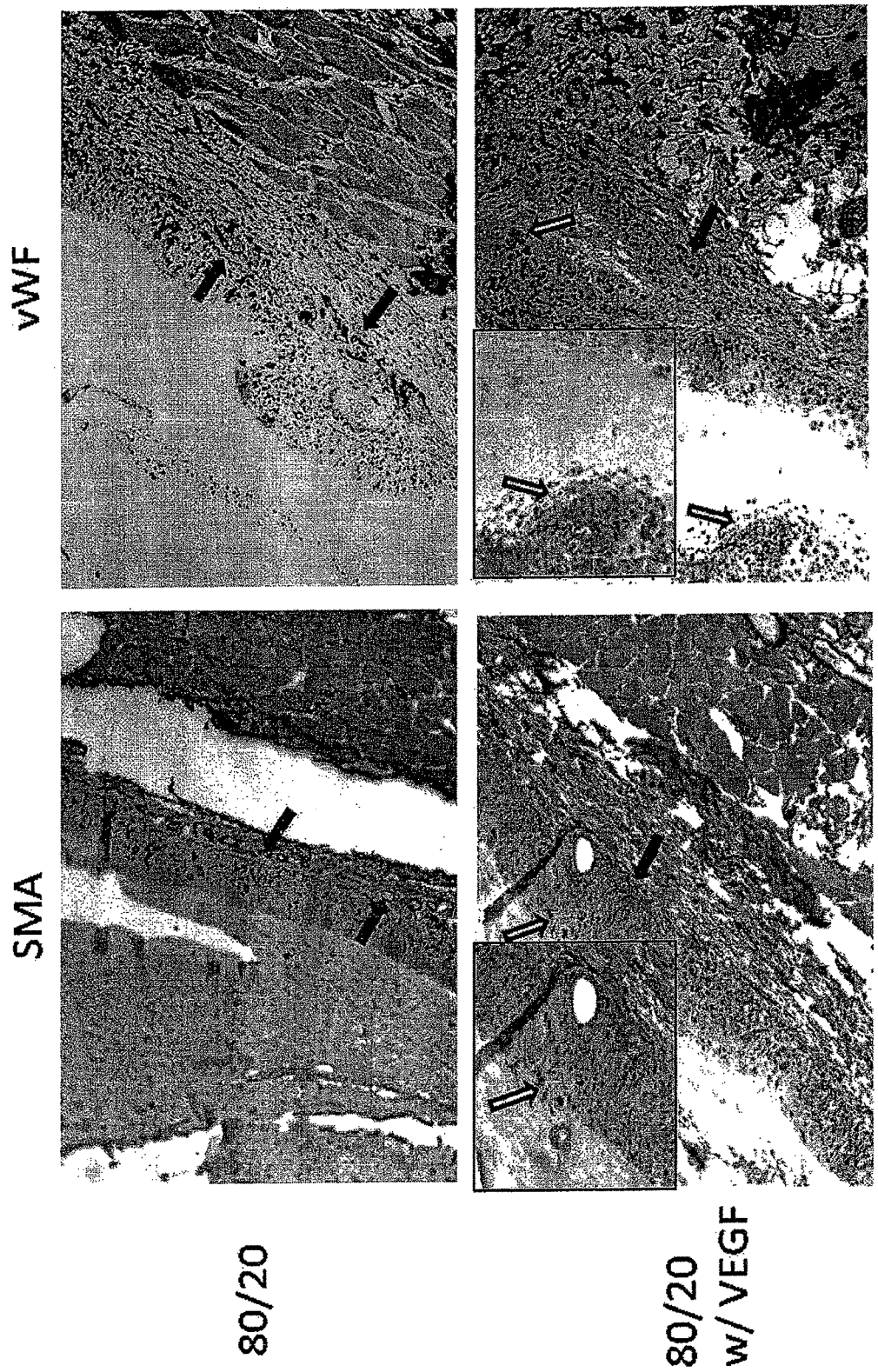
FIG. 10 shows low degree of substitution Dex-AE/PEGDA, ratio 80/20, at week 3 stained with SMA and vWF to identify the vasculature networks (solid arrows). Several vasculatures (no fill arrows) are observed inside the gel with VEGF encapsulation compared with no VEGF encapsulation which only shows vessel formation at the outside periphery of the gel.

The above study indicates the hydrogel at the ratio of 80/20 is a good candidate for soft tissue engineering. To examine this, the vasculogenesis capability of an 80/20 hydrogel was examined. FIG. 10 shows Dex-AE/PEGDA at the ratio 80/20 within 3 weeks stained with SMA and vWF to identify the vasculature networks (solid arrows). Several vasculatures (no fill arrows) are observed inside the hydrogel with VEGF encapsulation compared with no VEGF encapsulation, which only shows vessels formation at the outside periphery of the hydrogel. Unlike previous studies, which only demonstrated that VEGF promote tissue ingrowth, this study further indicates the VEGF can attract endothelial cells into the hydrogel and promote vascular formation.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A crosslinked hydrogel composition comprising
at least 80% of a polysaccharide with at least one monomer having at least one substituted hydroxyl group, wherein the substituted hydroxyl group has the formula (III), and wherein the degree of substitution of formula (III) on the polysaccharide is less than about 0.2; and polyethylene glycol diacrylate,
wherein
formula (III) is

—$O_1$—C(O)N$R^7$—$CH_2CH$=$CH_2$ and $O_1$ is the oxygen atom of said substituted hydroxyl group and $R^7$ is hydrogen or $C_1$-$C_4$ alkyl,
wherein the polysaccharide is dextran, and
wherein the polysaccharide is crosslinked by reaction with the poly(ethylene glycol) diacrylate.

2. The composition of claim 1, wherein $R^7$ is hydrogen.

3. The composition of claim 1, wherein the polysaccharide further comprises a second substituted hydroxyl group having the formula (IV), where formula (III) and formula (IV) are different, and the substituted hydroxyl group of formula (III) and formula (IV) may be on the same or different monomers; wherein formula (IV) is Y—(C$R^2R^3$)$_n$—Z where Y is –$O_1$- or —$O_1$C(O)—, or —$O_1$C(O)N$R^1$—, $O_1$ is the oxygen atom of said substituted hydroxyl group, and $R^1$ is hydrogen or $C_1$-$C_4$ alkyl; n=1, 2, 3, or 4; Z is selected from the group consisting of —$CO_2$H or N$R^4R^5$, where $R^4$ and $R^5$ are independently hydrogen or $C_1$-$C_4$ alkyl;
$R^2$ and $R^3$ are independently hydrogen, $C_1$-$C_4$ alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring.

4. The composition of claim 1, wherein the dextran has an average molecular weight of at least 20,000.

5. The composition of claim 1, wherein the poly(ethylene glycol) diacrylate has a molecular weight of at least 2000.

6. The composition of claim 1, further comprising a protein, oligonucleotide or pharmaceutical agent.

7. The composition of claim 6, comprising a protein, wherein the protein is a growth factor.

8. The composition of claim 7, wherein the growth factor is vascular endothelial growth factor (VEGF).

9. A method of delivering a protein, oligonucleotide or pharmaceutical agent to a subject in need of treatment with the protein, oligonucleotide or pharmaceutical agent, comprising administering to the subject a composition of claim 6.

10. The method of claim 9, wherein the composition is administered subcutaneously, or applied topically.

11. A method of increasing vascular regeneration comprising administering to a subject in need thereof a composition according to claim 6 comprising a protein that stimulates vascular regeneration.

12. The method of claim 11, wherein the protein is vascular endothelial growth factor (VEGF).

13. A crosslinked composition comprising
a polysaccharide with at least one monomer having at least one substituted hydroxyl group,
wherein the polysaccharide is crosslinked by reaction with poly(ethylene glycol) diacrylate; and
wherein the polysaccharide includes a first substituted hydroxyl group of formula (I) and a second substituted hydroxyl group of formula (II), wherein formula (I) and formula (II) are different, the degree of substitution of formula (I) on the polysaccharide is less than about 0.2; and the first and second substituted hydroxyl groups may be on the same or different monomer;
wherein
formula (I) is

—$O_1$—X where $O_1$ is the oxygen atom of said substituted hydroxyl group, and X is a crosslinkable moiety having a double bond; and formula (II) is

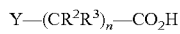

Y is $-O_1-$ or $-O_1C(O)-$, or $-O_1C(O)NR^1-$ where $O_1$ is the oxygen atom of said substituted hydroxyl group, and $R^1$ is hydrogen or $C_1$-$C_4$ alkyl, n=1, 2, 3, or 4, $R^2$ and $R^3$ may be independently hydrogen, $C_1$-$C_4$ alkyl, or may combine to form a 3-6 membered ring, and when n>1, $R^2$ and $R^3$ on different carbon atoms may form a 3-6 membered ring; and the polysaccharide is dextran.

14. The composition of claim 13, wherein the dextran has an average molecular weight of at least 20,000.

15. The composition of claim 13, wherein the crosslinkable moiety is derived from glycidyl acrylate, glycidyl methacrylate, methacrylate, acrylate, hydroxyethyl methacrylate, maleic anhydride, or allyl isocyanate.

16. The composition of claim 15, wherein formula (I) is

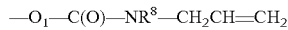

where $R^8$ is hydrogen or $C_1$-$C_4$ alkyl.

17. The composition of claim 13, wherein the poly(ethylene glycol) diacrylate has a molecular weight of at least 2000.

18. The composition of claim 13, wherein the composition is a hydrogel.

19. The composition of claim 13, further comprising a protein, oligonucleotide or pharmaceutical agent.

20. The composition of claim 19, comprising a protein, wherein the protein is a growth factor.

21. The composition of claim 20, wherein the growth factor is vascular endothelial growth factor (VEGF).

22. A method of delivering a protein, oligonucleotide or pharmaceutical agent to a subject in need of treatment with the protein, oligonucleotide or pharmaceutical agent, comprising administering to the subject a composition of claim 19.

23. The method of claim 22, wherein the composition comprises a protein.

24. The method of claim 23, wherein said protein is a growth factor.

25. The method of claim 24, wherein the protein is vascular endothelial growth factor (VEGF).

26. The method of claim 22 wherein the composition is administered subcutaneously, or applied topically.

27. A method of increasing vascular regeneration comprising administering to a subject in need thereof a composition according to claim 19 comprising a protein that stimulates vascular regeneration.

28. The method of claim 27, wherein said protein is a growth factor.

29. The method of claim 28, wherein the protein is vascular endothelial growth factor (VEGF).

30. The method of claim 27 wherein the composition is administered subcutaneously, or applied topically.

31. A method for sustained release of a therapeutic protein to a subject in need of treatment comprising administering a hydrogel according to claim 22 to the subject.

* * * * *